(12) United States Patent
Yamanaka et al.

(10) Patent No.: US 9,528,092 B2
(45) Date of Patent: Dec. 27, 2016

(54) METHODS OF EFFICIENTLY ESTABLISHING INDUCED PLURIPOTENT STEM CELLS UNDER HYPOXIC CONDITIONS

(75) Inventors: Shinya Yamanaka, Kyoto (JP); Yoshinori Yoshida, Kyoto (JP)

(73) Assignee: Kyoto University, Kyoto (JP)

( * ) Notice: Subject to any disclaimer, the term of this patent is extended or adjusted under 35 U.S.C. 154(b) by 124 days.

(21) Appl. No.: 12/672,222

(22) PCT Filed: Jul. 30, 2009

(86) PCT No.: PCT/JP2009/063906
§ 371 (c)(1),
(2), (4) Date: Apr. 1, 2010

(87) PCT Pub. No.: WO2010/013845
PCT Pub. Date: Feb. 4, 2010

(65) Prior Publication Data
US 2011/0039338 A1   Feb. 17, 2011

Related U.S. Application Data

(60) Provisional application No. 61/084,842, filed on Jul. 30, 2008, provisional application No. 61/141,177, filed on Dec. 29, 2008, provisional application No. 61/203,931, filed on Dec. 30, 2008.

(51) Int. Cl.
*C12N 15/87*  (2006.01)
*C12N 5/074*  (2010.01)

(52) U.S. Cl.
CPC ......... *C12N 5/0696* (2013.01); *C12N 2500/02* (2013.01); *C12N 2501/602* (2013.01); *C12N 2501/603* (2013.01); *C12N 2501/604* (2013.01); *C12N 2501/606* (2013.01); *C12N 2510/00* (2013.01)

(58) Field of Classification Search
CPC .............. C12N 15/87; C12N 2501/602; C12N 2501/606; C12N 2501/603; C12N 2510/00; C12N 2501/604; C12N 2500/02; C12N 5/0696
See application file for complete search history.

(56) References Cited

U.S. PATENT DOCUMENTS

| | | |
|---|---|---|
| 8,058,065 B2 | 11/2011 | Yamanaka et al. |
| 8,530,238 B2 | 9/2013 | Yamanaka et al. |
| 2009/0047263 A1 | 2/2009 | Yamanaka et al. |
| 2009/0068742 A1 | 3/2009 | Yamanaka |
| 2009/0227032 A1 | 9/2009 | Yamanaka et al. |
| 2010/0279404 A1 | 11/2010 | Yamanaka et al. |
| 2011/0231944 A1 | 9/2011 | Watarai et al. |
| 2011/0236362 A1 | 9/2011 | Watarai et al. |
| 2012/0196360 A1 | 8/2012 | Okita et al. |
| 2013/0065311 A1 | 3/2013 | Yamanaka et al. |

FOREIGN PATENT DOCUMENTS

| | | |
|---|---|---|
| WO | WO 99/20741 A1 | 4/1999 |
| WO | WO 2004/055155 A2 | 7/2004 |
| WO | WO 2006/019366 A1 | 2/2006 |
| WO | WO 2006/029198 A2 | 3/2006 |
| WO | WO 2006/073911 A1 | 7/2006 |
| WO | WO 2007/069666 A1 | 6/2007 |
| WO | WO 2008/084401 A2 | 7/2008 |
| WO | WO 2008/118820 A2 | 10/2008 |
| WO | WO 2009/032456 A2 | 3/2009 |
| WO | WO 2009/073523 A2 | 6/2009 |
| WO | WO 2009/111087 A1 | 9/2009 |
| WO | WO 2009/142717 A2 | 11/2009 |
| WO | WO 2009142717 A2 * | 11/2009 |
| WO | WO 2010/027062 A1 | 3/2010 |
| WO | WO 2010/027094 A1 | 3/2010 |

OTHER PUBLICATIONS

Hanley et al., British Journal of Hæmatology, 151: 16-24, 2010.*
Oliveri et al. Regenerative Medicine, 2(5): 795-816, Sep. 2007.*
Djuric and Ellis, Stem Cell Research and Therapy, 2010, 202: 1:3.*
Plath et al. Nature Reviews, 12: 253-265, 2011.*
Simon et al., Nature Reviews, Molecular Cell Biology, 9: 285-296, 2008.*
Robins et al., Bone, 37: 313-322, 2005.*
Lim et al. Proteomics, 2:1187-1203, 2002.*
Prowse et al. Proteomics, 5:978-989, 2005.*
Forsyth et al., Cloning and Stem Cells, 8(1): 16-23, 2006.*
Amit et al. Biol. of Reprod., 70: 837-845, 2004.*
Stadtfeld. Science, 322: 945-949, 2008.*
Okita. Science, 322: 949-953, 2008.*
Gonzalez. PNAS, 106(22): 8918-8922, 2009.*
Kim et al. Cell Stem Cell, 4(6): 472-476, 2009.*
Covello et al., *Genes & Dev.*, 20: 557-570 (2006).
Danet et al., *Journal of Clinical Investigation*, 112(1): 126-135 (Jul. 2003).
D'Ippolito et al., *Journal of Cell Science*, 117(14): 2971-2981 (2004).
Ezashi et al., *Proc. Natl. Acad. Sci.*, 102(13): 4783-4788 (Mar. 29, 2005).
Feng et al., *Nature Cell Biology*, 11(2): 197-203 (Feb. 2009).
Grayson et al., *Journal of Cellular Physiology*, 207: 331-339 (2006).
Grayson et al., *Biochemical and Biophysical Research Communications*, 358: 948-953 (2007).
Huangfu et al., *Nature Biotechnology*, 26(7): 795-797 (Jul. 2008).
Huangfu et al., *Nature Biotechnology*, 26(11): 1269-1275 (Nov. 2008).
Kaji et al., *Nature*, 458: 771-775 (Apr. 2009).
Kim et al., *Nature*, 454: 646-650 (Jul. 31, 2008).
Liao et al., *Cell Research*, 18: 600-603 (2008).

(Continued)

*Primary Examiner* — Thaian N Ton
(74) *Attorney, Agent, or Firm* — Leydig, Voit & Mayer, Ltd.

(57) ABSTRACT

Provided is a method of improving the efficiency of establishment of induced pluripotent stem cells, comprising culturing somatic cells under hypoxic conditions in the step of nuclear reprogramming thereof.

14 Claims, 17 Drawing Sheets
(17 of 17 Drawing Sheet(s) Filed in Color)

(56) References Cited

OTHER PUBLICATIONS

Maherali et al., *Cell Stem Cell*, 1: 55-70 (Jul. 2007).
Mali et al., *Stem Cells*, 26: 1998-2005 (2008).
Marson et al., *Cell Stem Cell*, 3: 132-135 (Aug. 7, 2008).
Morrison et al., *The Journal of Neuroscience*, 20(19): 7370-7376 (Oct. 1, 2000).
Nakagawa et al., *Nature Biotechnology*, 26(1): 101-106 (Jan. 2008).
Okita et al., *Nature*: 448: 313-317 (Jul. 19, 2007).
Okita et al., *Science*, 322: 949-953 (2008).
Page et al., *Cloning and Stem Cells*, 11(3): 417-426 (2009).
Park et al., *Nature*, 451: 141-146 (Jan. 2008).
Silva et al., *PLoS Biology*, 6(10): 2237-2247 (Oct. 2008).
Shi et al., *Cell Stem Cell*, 2: 525-528 (Jun. 2008).
Shi et al., *Cell Stem Cell*, 3: 568-574 (Nov. 6, 2008).
Takahashi et al., *Cell*, 126, 663-676 (Aug. 25, 2006).
Takahashi et al., *Cell*, 131: 861-872 (Nov. 30, 2007).
Wernig et al., *Nature*, 448: 318-324 (Jul. 19, 2007).
Woltjen et al., *Nature*, 458: 766-770 (Apr. 9, 2009).
Yoshida et al., *Cell Stem Cell*, 5: 237-241 (Sep. 4, 2009).
Yu et al., *Science*, 318: 1917-1920 (2007).
Yu et al., *Science*, 324: 797-801 (2009).
Zhao et al., *Cell Stem Cell*, 3: 475-479 (Nov. 6, 2008).
He et al., *Journal of Experimental Hematology*, 15(2): 433-436 (2007).
Chinese Patent Office, First Office Action in Chinese Patent Application No. 200980100065 (Mar. 20, 2012).
Li et al., *Biotechnology and Bioengineering*, 91(6): 688-698 (2005).
International Bureau of WIPO, International Preliminary Report on Patentability in International Patent Application No. PCT/JP2009/063906 (Feb. 1, 2011).
Japanese Patent Office, International Search Report in International Patent Application No. PCT/JP2009/063906 (Nov. 2, 2009).
Chinese Patent Office, Second Office Action in Chinese Patent Application No. 200980100065 (Sep. 13, 2012).
European Patent Office, Supplementary European Search Report in European Patent Application No. 09803075.2 (Sep. 21, 2012).
Keith et al., *Cell*, 129(3): 465-472 (May 4, 2007).
Millman et al., *Current Opinion in Organ Transplantation*, 14(6): 694-700 (Dec. 1, 2009).
Powers et al., *Biotechnology and Bioengineering*, 101(2): 241-254 (Oct. 1, 2008).
Iida et al., *J. Dent. Res.*, 92(10): 905-910 (2013).
Shimada et al., *Biochem. Biophys. Res. Commun.*, 417: 659-664 (2012).
DeFoort et al., *Mol. Pharmacol.*, 69(4): 1304-1310 (2006).

\* cited by examiner

Fig. 13
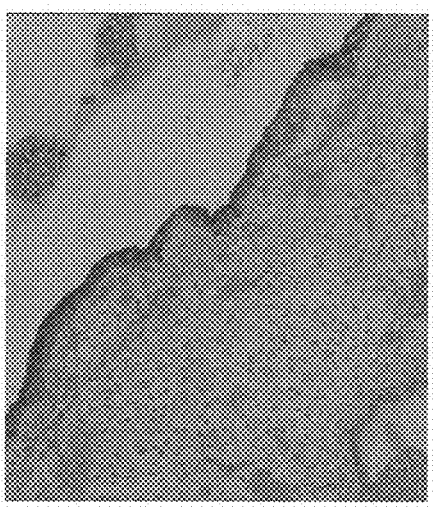
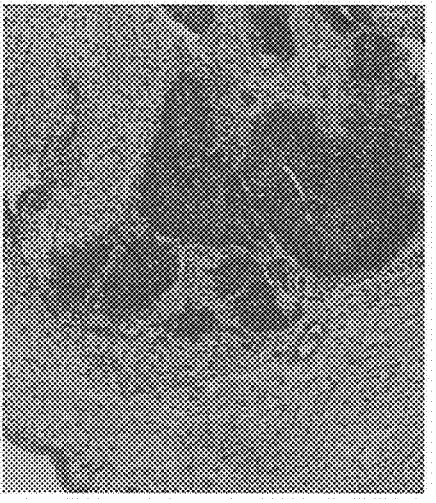
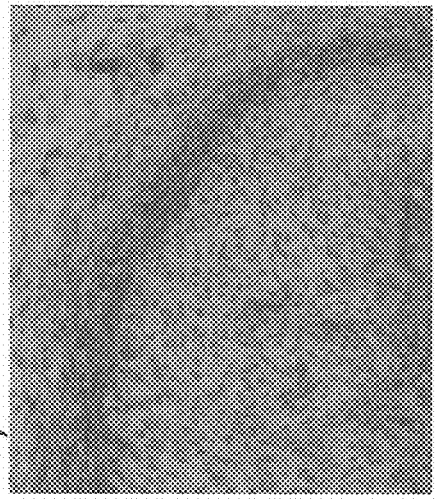

Fig. 18
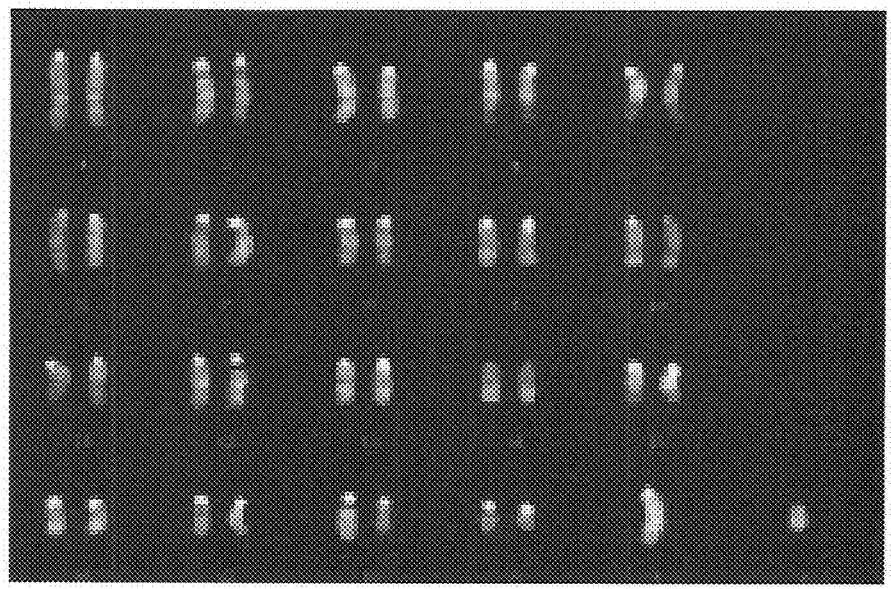
Fig. 19
a) 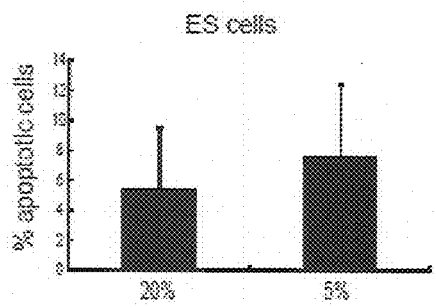
b) 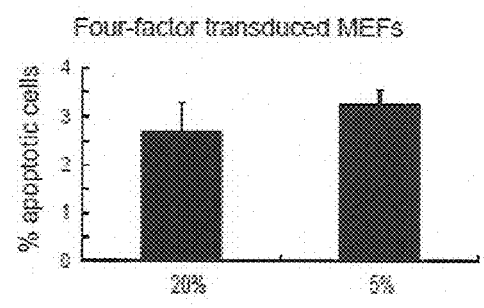

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: Primer (mouse c-Myc (end))

<400> SEQUENCE: 1
cagaggagga acgagctgaa gcgc                                          24

<210> SEQ ID NO 2
<211> LENGTH: 28
<212> TYPE: DNA
<213> ORGANISM: Artificial Sequence
<220> FEATURE:
<223> OTHER INFORMATION: Primer (mouse c-Myc (end))

<400> SEQUENCE: 2
ttatgcacca gagtttcgaa gctgttcg                                      28

<210> SEQ ID NO 3
<211> LENGTH: 23
<212> TYPE: DNA
<213> ORGANISM: Artificial Sequence
<220> FEATURE:
<223> OTHER INFORMATION: Primer (mouse Oct3/4 (end))

<400> SEQUENCE: 3
tctttccacc aggcccccgg ctc                                           23

<210> SEQ ID NO 4
<211> LENGTH: 23
<212> TYPE: DNA
<213> ORGANISM: Artificial Sequence
<220> FEATURE:
<223> OTHER INFORMATION: Primer (mouse Oct3/4 (end))

<400> SEQUENCE: 4
tgcgggcgga catggggaga tcc                                           23

<210> SEQ ID NO 5
<211> LENGTH: 23
<212> TYPE: DNA
<213> ORGANISM: Artificial Sequence
<220> FEATURE:
<223> OTHER INFORMATION: Primer (mouse Sox2 (end))

<400> SEQUENCE: 5
tagagctaga ctccgggcga tga                                           23

<210> SEQ ID NO 6
<211> LENGTH: 23
<212> TYPE: DNA
<213> ORGANISM: Artificial Sequence
<220> FEATURE:
<223> OTHER INFORMATION: Primer (mouse Sox2 (end))

<400> SEQUENCE: 6 ttgcccttaaa caagaccacg aaa                                          23

<210> SEQ ID NO 7
<211> LENGTH: 23
<212> TYPE: DNA
<213> ORGANISM: Artificial Sequence
```

```
<220> FEATURE:
<223> OTHER INFORMATION: Primer (mouse Klf4 (end))

<400> SEQUENCE: 7
ccaacttgaa catgcccgga ctt                                           23

<210> SEQ ID NO 8
<211> LENGTH: 23
<212> TYPE: DNA
<213> ORGANISM: Artificial Sequence
<220> FEATURE:
<223> OTHER INFORMATION: Primer (mouse Klf4 (end))

<400> SEQUENCE: 8
tctgcttaaa ggcatacttg gga                                           23

<210> SEQ ID NO 9
<211> LENGTH: 24
<212> TYPE: DNA
<213> ORGANISM: Artificial Sequence
<220> FEATURE:
<223> OTHER INFORMATION: Primer (mouse Oct3/4 (Tg))

<400> SEQUENCE: 9
ttgggctaga gaaggatgtg gttc                                          24

<210> SEQ ID NO 10
<211> LENGTH: 24
<212> TYPE: DNA
<213> ORGANISM: Artificial Sequence
<220> FEATURE:
<223> OTHER INFORMATION: Primer (mouse Oct3/4 (Tg))

<400> SEQUENCE: 10
gacatggcct gcccggttat tatt                                          24

<210> SEQ ID NO 11
<211> LENGTH: 21
<212> TYPE: DNA
<213> ORGANISM: Artificial Sequence
<220> FEATURE:
<223> OTHER INFORMATION: Primer (mouse Nanog)

<400> SEQUENCE: 11
agggtctgct actgagatgc t                                             21

<210> SEQ ID NO 12
<211> LENGTH: 24
<212> TYPE: DNA
<213> ORGANISM: Artificial Sequence
<220> FEATURE:
<223> OTHER INFORMATION: Primer (mouse Nanog)

<400> SEQUENCE: 12
caacacctgg tttttctgcc accg                                          24

<210> SEQ ID NO 13
<211> LENGTH: 24
<212> TYPE: DNA
<213> ORGANISM: Artificial Sequence
<220> FEATURE:
<223> OTHER INFORMATION: Primer (mouse Rex1)

<400> SEQUENCE: 13
acgagtggca gtttcttctt ggga                                          24
```

```
<210> SEQ ID NO 14
<211> LENGTH: 24
<212> TYPE: DNA
<213> ORGANISM: Artificial Sequence
<220> FEATURE:
<223> OTHER INFORMATION: Primer (mouse Rex1)

<400> SEQUENCE: 14
tatgactcac ttccaggggg cact                                              24

<210> SEQ ID NO 15
<211> LENGTH: 28
<212> TYPE: DNA
<213> ORGANISM: Artificial Sequence
<220> FEATURE:
<223> OTHER INFORMATION: Primer (mouse ECAT1)

<400> SEQUENCE: 15
tgtggggccc tgaaaggcga gctgagat                                          28

<210> SEQ ID NO 16
<211> LENGTH: 28
<212> TYPE: DNA
<213> ORGANISM: Artificial Sequence
<220> FEATURE:
<223> OTHER INFORMATION: Primer (mouse ECAT1)

<400> SEQUENCE: 16
atgggccgcc atacgacgac gctcaact                                          28

<210> SEQ ID NO 17
<211> LENGTH: 20
<212> TYPE: DNA
<213> ORGANISM: Artificial Sequence
<220> FEATURE:
<223> OTHER INFORMATION: Primer (mouse G3PDH)

<400> SEQUENCE: 17
accacagtcc atgccatcac                                                   20

<210> SEQ ID NO 18
<211> LENGTH: 20
<212> TYPE: DNA
<213> ORGANISM: Artificial Sequence
<220> FEATURE:
<223> OTHER INFORMATION: Primer (mouse G3PDH)

<400> SEQUENCE: 18
tccaccaccc tgttgctgta                                                   20

<210> SEQ ID NO 19
<211> LENGTH: 26
<212> TYPE: DNA
<213> ORGANISM: Artificial Sequence
<220> FEATURE:
<223> OTHER INFORMATION: Primer (human c-Myc (end))

<400> SEQUENCE: 19
gcgtcctggg aagggagatc cggagc                                            26

<210> SEQ ID NO 20
<211> LENGTH: 26
<212> TYPE: DNA
<213> ORGANISM: Artificial Sequence
<220> FEATURE:
<223> OTHER INFORMATION: Primer (human c-Myc (end))
```

<400> SEQUENCE: 20
ttgaggggca tcgtcgcggg aggctg                                      26

<210> SEQ ID NO 21
<211> LENGTH: 24
<212> TYPE: DNA
<213> ORGANISM: Artificial Sequence
<220> FEATURE:
<223> OTHER INFORMATION: Primer (human Oct3/4 (end))

<400> SEQUENCE: 21
gacaggggga ggggaggagc tagg                                        24

<210> SEQ ID NO 22
<211> LENGTH: 26
<212> TYPE: DNA
<213> ORGANISM: Artificial Sequence
<220> FEATURE:
<223> OTHER INFORMATION: Primer (human Oct3/4 (end))

<400> SEQUENCE: 22
cttccctcca accagttgcc ccaaac                                      26

<210> SEQ ID NO 23
<211> LENGTH: 26
<212> TYPE: DNA
<213> ORGANISM: Artificial Sequence
<220> FEATURE:
<223> OTHER INFORMATION: Primer (human Sox2 (end))

<400> SEQUENCE: 23
gggaaatggg aggggtgcaa aagagg                                      26

<210> SEQ ID NO 24
<211> LENGTH: 26
<212> TYPE: DNA
<213> ORGANISM: Artificial Sequence
<220> FEATURE:
<223> OTHER INFORMATION: Primer (human Sox2 (end))

<400> SEQUENCE: 24
ttgcgtgagt gtggatggga ttggtg                                      26

<210> SEQ ID NO 25
<211> LENGTH: 25
<212> TYPE: DNA
<213> ORGANISM: Artificial Sequence
<220> FEATURE:
<223> OTHER INFORMATION: Primer (human Klf4 (end))

<400> SEQUENCE: 25
acgatcgtgg ccccggaaaa ggacc                                       25

<210> SEQ ID NO 26
<211> LENGTH: 28
<212> TYPE: DNA
<213> ORGANISM: Artificial Sequence
<220> FEATURE:
<223> OTHER INFORMATION: Primer (human Klf4 (end))

<400> SEQUENCE: 26
tgattgtagt gctttctggc tgggctcc                                    28

<210> SEQ ID NO 27
<211> LENGTH: 25
<212> TYPE: DNA
<213> ORGANISM: Artificial Sequence
<220> FEATURE:
<223> OTHER INFORMATION: Primer (human Nanog)

<400> SEQUENCE: 27
cagccccgat tcttccacca gtccc                                   25

<210> SEQ ID NO 28
<211> LENGTH: 25
<212> TYPE: DNA
<213> ORGANISM: Artificial Sequence
<220> FEATURE:
<223> OTHER INFORMATION: Primer (human Nanog)

<400> SEQUENCE: 28
cggaagattc ccagtcgggt tcacc                                   25

<210> SEQ ID NO 29
<211> LENGTH: 24
<212> TYPE: DNA
<213> ORGANISM: Artificial Sequence
<220> FEATURE:
<223> OTHER INFORMATION: Primer (human GDF3)

<400> SEQUENCE: 29
cttatgctac gtaaaggagc tggg                                    24

<210> SEQ ID NO 30
<211> LENGTH: 21
<212> TYPE: DNA
<213> ORGANISM: Artificial Sequence
<220> FEATURE:
<223> OTHER INFORMATION: Primer (human GDF3)

<400> SEQUENCE: 30
ccaacccagg tcccggaagt t                                       21

<210> SEQ ID NO 31
<211> LENGTH: 24
<212> TYPE: DNA
<213> ORGANISM: Artificial Sequence
<220> FEATURE:
<223> OTHER INFORMATION: Primer (human ESG1)

<400> SEQUENCE: 31
atatcccgcc gtgggtgaaa gttc                                    24

<210> SEQ ID NO 32
<211> LENGTH: 24
<212> TYPE: DNA
<213> ORGANISM: Artificial Sequence
<220> FEATURE:
<223> OTHER INFORMATION: Primer (human ESG1)

<400> SEQUENCE: 32
actcagccat ggactggagc atcc                                    24

<210> SEQ ID NO 33
<211> LENGTH: 24
<212> TYPE: DNA
<213> ORGANISM: Artificial Sequence
<220> FEATURE:
<223> OTHER INFORMATION: Primer (human Rex1)

```
<400> SEQUENCE: 33
cagatcctaa acagctcgca gaat                                          24

<210> SEQ ID NO 34
<211> LENGTH: 23
<212> TYPE: DNA
<213> ORGANISM: Artificial Sequence
<220> FEATURE:
<223> OTHER INFORMATION: Primer (human Rex1)

<400> SEQUENCE: 34
gcgtacgcaa attaaagtcc aga                                           23

<210> SEQ ID NO 35
<211> LENGTH: 20
<212> TYPE: DNA
<213> ORGANISM: Artificial Sequence
<220> FEATURE:
<223> OTHER INFORMATION: Primer (human G3PDH)

<400> SEQUENCE: 35
accacagtcc atgccatcac                                               20

<210> SEQ ID NO 36
<211> LENGTH: 20
<212> TYPE: DNA
<213> ORGANISM: Artificial Sequence
<220> FEATURE:
<223> OTHER INFORMATION: Primer (human G3PDH)

<400> SEQUENCE: 36
tccaccaccc tgttgctgta                                               20
```

METHODS OF EFFICIENTLY ESTABLISHING INDUCED PLURIPOTENT STEM CELLS UNDER HYPOXIC CONDITIONS

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,416 bytes ASCII (Text) file named "706075SequenceListing.txt," created Feb. 4, 2010.

TECHNICAL FIELD OF THE INVENTION

The present invention relates to a method of improving the efficiency of establishment of induced pluripotent stem (hereinafter referred to as iPS) cells. More specifically, the present invention relates to a method of improving the efficiency of establishment of iPS cells, comprising culturing somatic cells in hypoxic conditions in the step of nuclear reprogramming thereof.

BACKGROUND OF THE INVENTION

In recent years, mouse and human iPS cells have been established one after another. Yamanaka et al. induced iPS cells by introducing the Oct3/4, Sox2, Klf4 and c-Myc genes into fibroblasts from a reporter mouse wherein the neomycin resistance gene is knocked-in into the Fbx15 locus, and forcing the cells to express the genes (1,2). Okita et al. (3) succeeded in establishing iPS cells (Nanog iPS cells) that show almost the same gene expression and epigenetic modification profiles as those in embryonic stem (ES) cells by producing a transgenic mouse wherein the green fluorescent protein (GFP) and puromycin-resistance genes are integrated into the locus of Nanog, whose expression is more localized in pluripotent cells than Fbx15 expression, forcing fibroblasts derived from the mouse to express the above-mentioned four genes, and selecting puromycin-resistant and GFP-positive cells. Similar results were obtained by other groups (4,5). Thereafter, it was revealed that iPS cells could also be produced with three factors other than the c-Myc gene (6).

Furthermore, Yamanaka et al. succeeded in establishing iPS cells by introducing the same four genes as those used in the mouse into human skin fibroblasts (1,7). On the other hand, a group of Thomson et al. produced human iPS cells using Nanog and Lin28 in place of Klf4 and c-Myc (8,9). Park et al. (10) produced human iPS cells using TERT, which is known as the human cell immortalizing gene, and the SV40 large T antigen, in addition to the four factors Oct3/4, Sox2, Klf4 and c-Myc. Hence, it has been demonstrated that iPS cells comparable to ES cells in terms of pluripotency can be produced in both humans and mice, by introducing defined factors into somatic cells.

However, the efficiency of iPS cell establishment is low at less than 1%. Especially, a problem of extremely low efficiency of iPS cell establishment arises when they are produced by introducing three factors (Oct3/4, Sox2, Klf4) other than c-Myc, which is feared to cause tumorigenesis in tissues and individuals differentiated from iPS cells, into somatic cells.

By the way, some reports are available on the association between the maintenance of the undifferentiated state and pluripotency of cells and hypoxic conditions. Ezashi et al. (11) observed that human ES (hES) cells cultured under hypoxic conditions had their differentiation suppressed, suggesting the necessity of cultivation under hypoxic conditions to maintain sufficient pluripotency for hES cells. Covello et al. (12) showed that a transcription regulatory factor induced early under hypoxic conditions (HIF-2α) was capable of inducing the expression of Oct3/4 and regulating the functions and differentiation of stem cells. Furthermore, Grayson et al. (13,14) showed that hypoxic conditions were involved in the maintenance of the undifferentiated state and pluripotency of human mesenchymal stem cells (hMSCs). However, no report is available on the relationship between the nuclear reprogramming process in somatic cells that have once differentiated and hypoxic conditions.

REFERENCES CITED

1. WO 2007/069666 A1
2. Takahashi, K. and Yamanaka, S., *Cell,* 126: 663-676 (2006)
3. Okita, K. et al., *Nature,* 448: 313-317 (2007)
4. Wernig, M. et al., *Nature,* 448: 318-324 (2007)
5. Maherali, N. et al., *Cell Stem Cell,* 1: 55-70 (2007)
6. Nakagawa, M. et al., *Nat. Biotethnol.,* 26: 101-106 (2008)
7. Takahashi, K. et al., *Cell,* 131: 861-872 (2007)
8. WO 2008/118820 A2
9. Yu, J. et al., *Science,* 318: 1917-1920 (2007)
10. Park, I. H. et al., *Nature,* 451: 141-146 (2008)
11. Ezashi, T. et al., *Proc. Natl. Acad. Sci. USA,* 102: 4783-4788 (2005)
12. Covello, K. L. et al., *Genes & Dev.,* 20: 557-570 (2006)
13. Grayson, W. L. et al., *J. Cell. Physiol.,* 207:331-339 (2006)
14. Grayson, W. L. et al., *Biochem. Biophys. Res. Commun.,* 358: 948-953 (2007)

SUMMARY OF THE INVENTION

It is an object of the present invention to provide a means of improving the efficiency of establishment of iPS cells, and to provide a method of efficiently producing iPS cells using the means.

The present inventors conducted extensive investigations with the aim of accomplishing the above-described object and succeeded in dramatically improving the efficiency of establishment of iPS cells, and have developed the present invention.

Accordingly, the present invention provides:

[1] A method of improving the efficiency of establishment of iPS cells, comprising culturing somatic cells under hypoxic conditions in the step of nuclear reprogramming thereof.

[2] The method of [1] above, wherein the oxygen concentration in the ambient atmosphere is between 1% and 10%.

[3] The method of [2] above, wherein the oxygen concentration in the ambient atmosphere is between 1% and 5%.

[4] The method according to any one of [1] to [3] above, wherein the nuclear reprogramming substances are the following substances, or nucleic acids that encode the same;
  (i) Oct3/4 and Klf4, or
  (ii) Oct3/4 and c-Myc, or
  (iii) Oct3/4, Klf4 and Sox2, or
  (iv) Oct3/4, Klf4 and c-Myc, or
  (v) Oct3/4, Klf4, Sox2 and c-Myc.

[5] The method according to any one of [1] to [4] above, comprising the further step that valproic acid is used as efficiency improver in the step of nuclear reprogramming.

[6] The method according to any one of [1] to [5] above, wherein culturing somatic cells under hypoxic conditions is performed for more than 3 days after contacting a nuclear reprogramming substance.

Because hypoxic conditions in the step of nuclear reprogramming make it possible to increase the efficiency of establishment of iPS cells remarkably, the same are particularly useful in the induction of iPS cells by means of three factors except c-Myc or Sox2, which has traditionally been associated with very low efficiency of iPS cell establishment. The same are also useful in the induction of iPS cells by means of two factors (e.g., Oct3/4 and Klf4; Oct3/4 and c-Myc). Because c-Myc, in particular, is feared to cause tumorigenesis when reactivated, the improvement in the efficiency of iPS cell establishment using two or three factors is of paramount utility in applying iPS cells to regenerative medicine. Because such hypoxic conditions can be created very easily using a widely-used $CO_2$ incubator that allows control of oxygen concentrations, iPS cells can be prepared efficiently without the need of painstaking steps or technical skills.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 4:
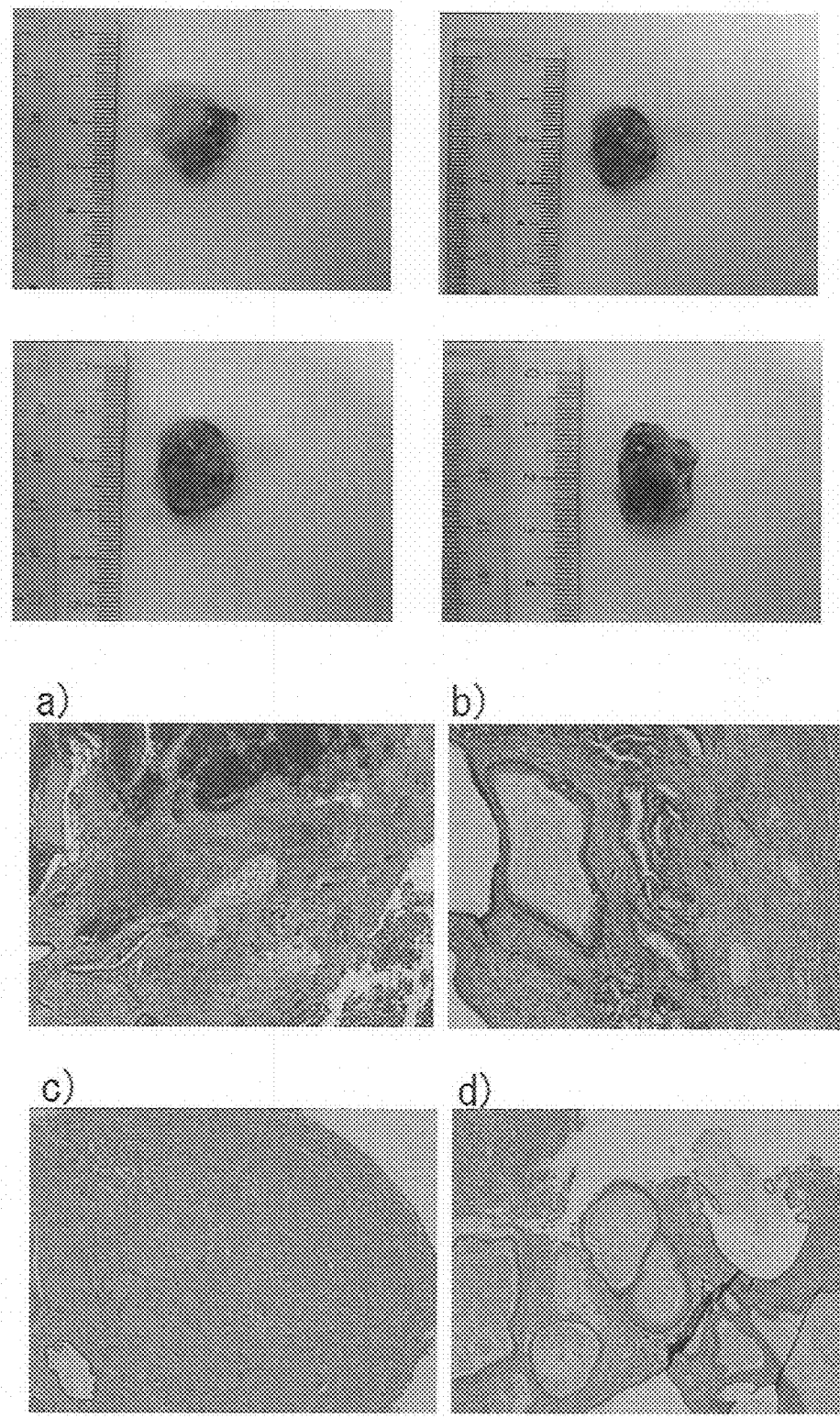

The upper pannels in FIG. 4 show photographs of teratomas formed by subcutaneously injecting mouse iPS cells (527CH5-2) established at a low oxygen concentration (5%) with Oct3/4 and Klf4 into immunodeficient mice. The lower pannels in FIG. 4 show histological staining images (hematoxylin-eosin staining) of the teratomas obtained [a): cartilage tissue, b): endodermal epithelial tissue, c): muscle tissue, d): keratinized epithelial tissue].

Figure 5:
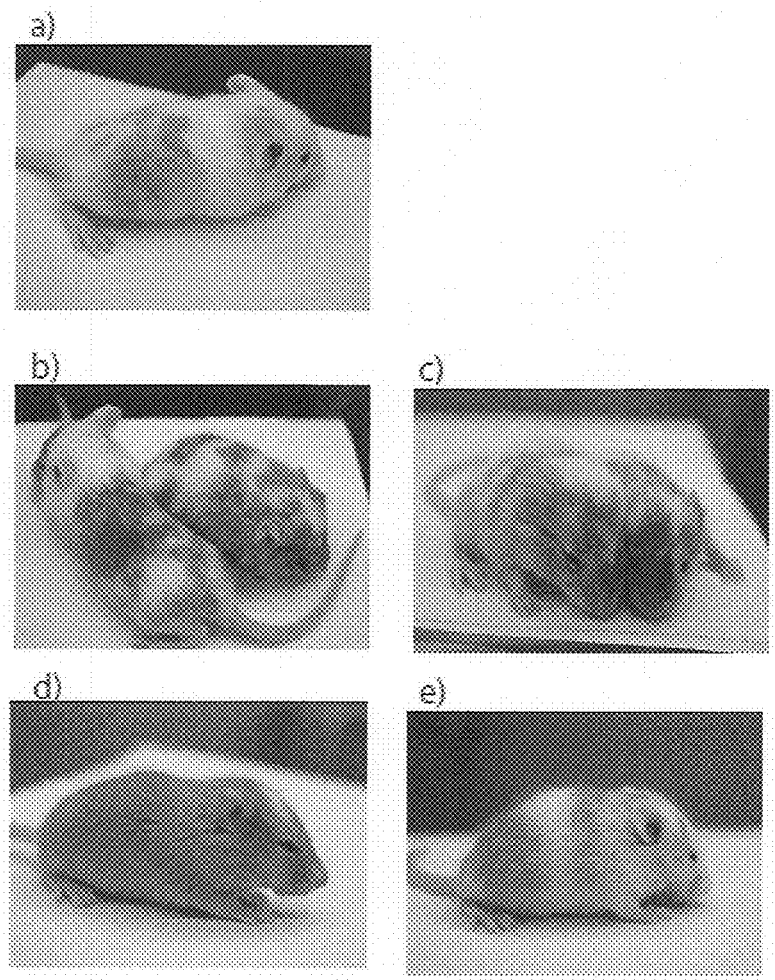

FIG. 5 shows photographs of adult chimeras created by microinjecting iPS cells established at a low oxygen concentration (5%) with the introduction of two, three or four genes, into blastocysts from ICR mice, taken at 2 weeks of age.
a): A chimeric mouse (male) derived from iPS cells established by introducing four genes (521AH5-1)
b): Chimeric mice (male) derived from iPS cells established by introducing three genes (535BH5-1)
c): Chimeric mice (female) derived from an iPS cell established by introducing three genes (535BH5-1)
d): A chimeric mouse (male) derived from iPS cells established by introducing two genes (527CH5-1)
e): A chimeric mouse (male) derived from iPS cells established by introducing two genes (527CH5-2)

Figure 6:
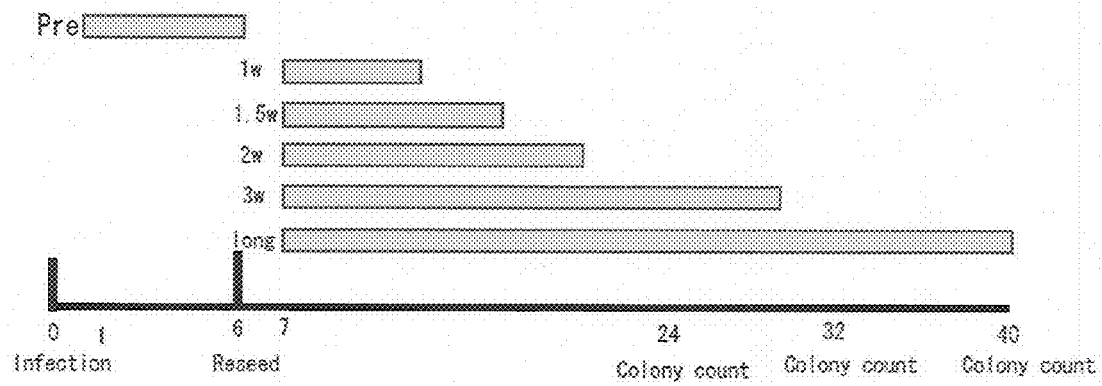

FIG. 6 shows the time schedule for Example 7.

Figure 7:
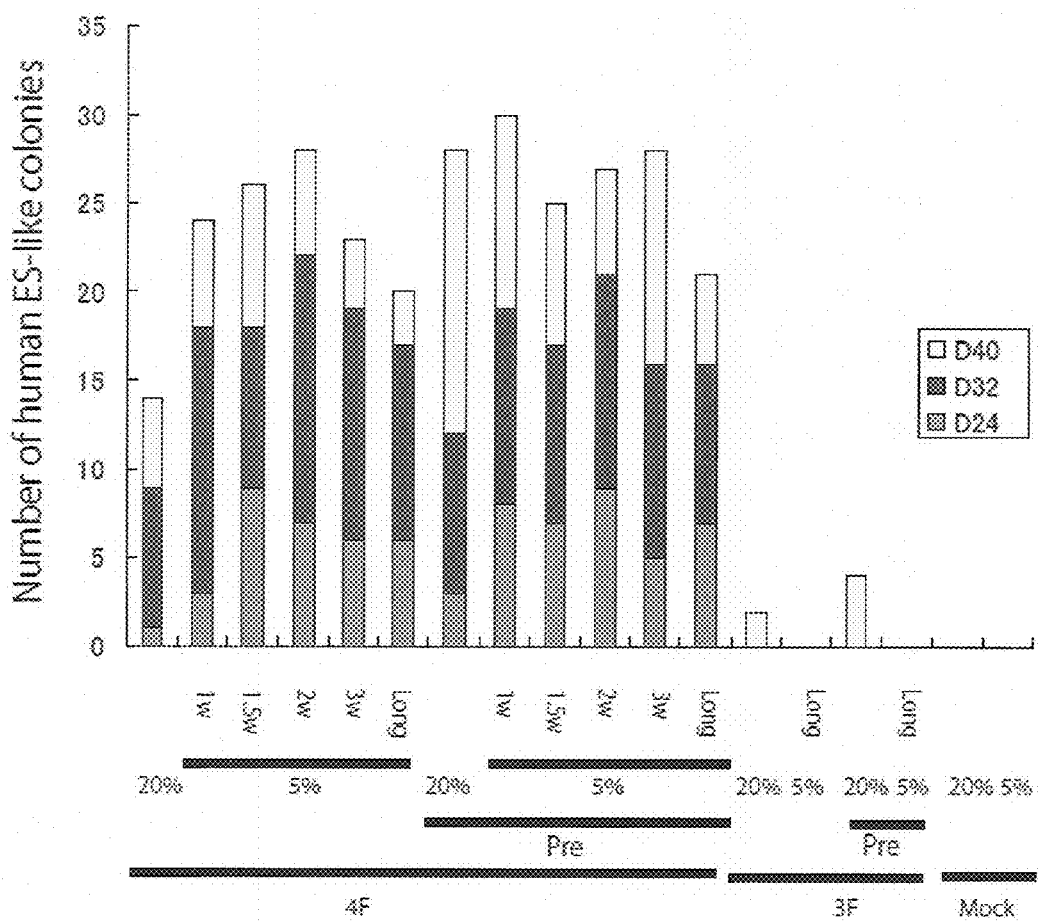

FIG. 7 is a graphic representation of the numbers of colonies of iPS cells established under the various culture conditions in Example 7. "Pre" shows the results obtained with pre-culture under hypoxic conditions. "4F", "3F", and "Mock" show the results obtained with the introduction of four genes (Oct3/4, Klf4, Sox2, c-Myc), three genes (Oct3/4, Klf4, Sox2), and an empty vector, respectively.

Figure 8:
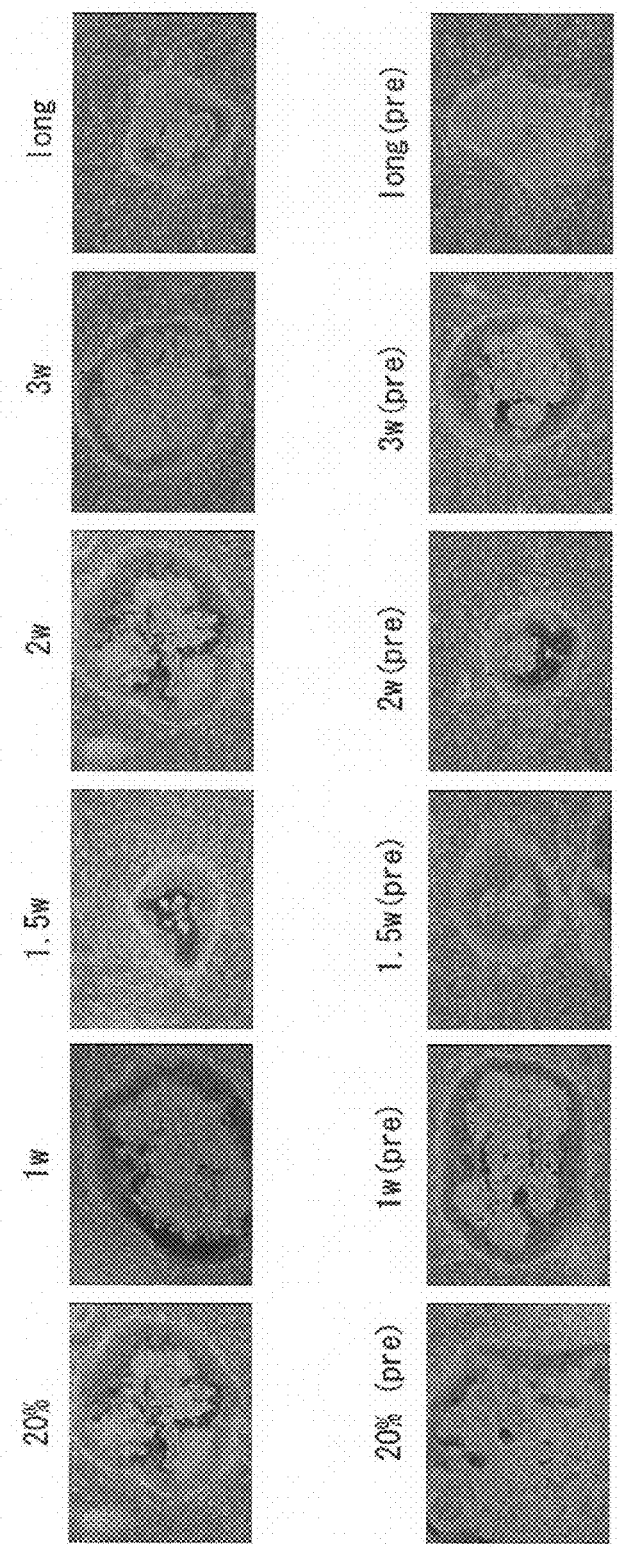

FIG. 8 is a photographic representation of the morphology of iPS cell colonies obtained with the introduction of four genes in Example 7, taken on day 40 after infection. The upper and lower pannels show images of colonies obtained under hypoxic conditions without pre-culture and those obtained under hypoxic conditions with pre-culture, respectively.

Figure 9:
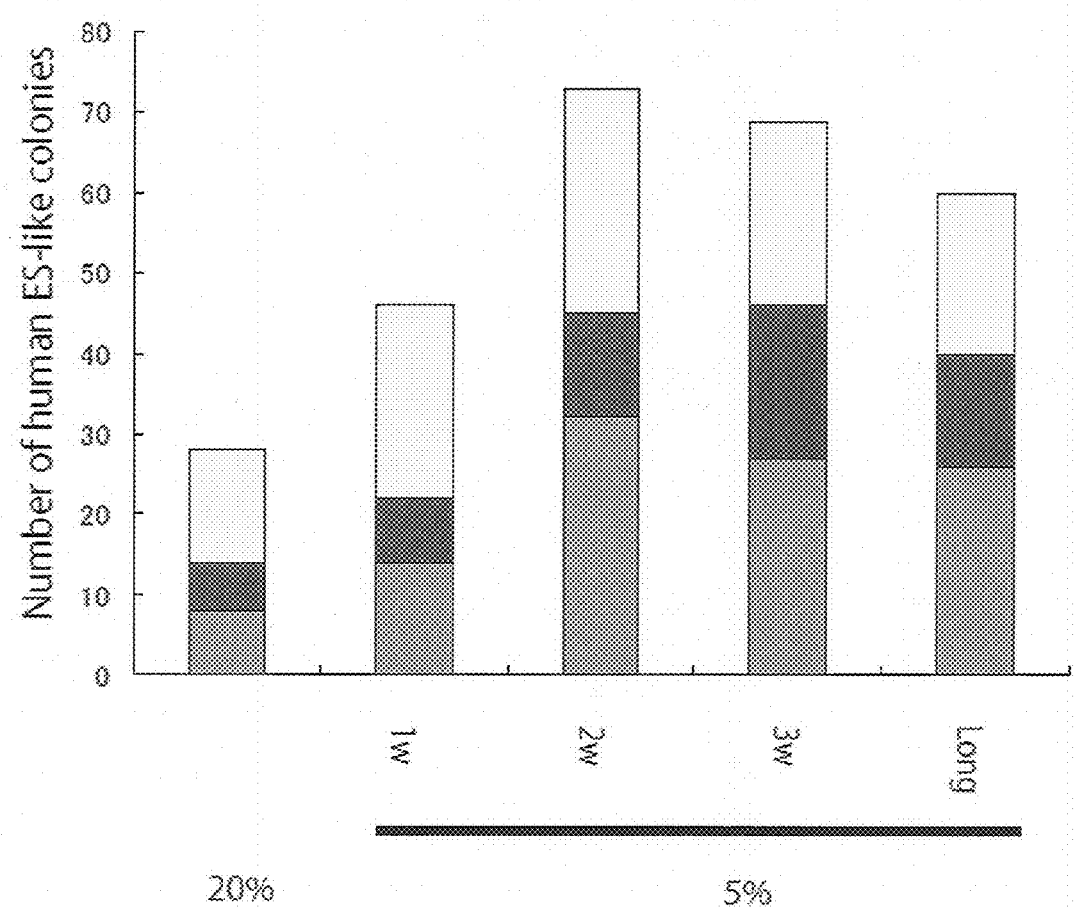

FIG. 9 is a graphic representation comparing the numbers of iPS cell colonies obtained by introducing four genes (Oct3/4, Klf4, Sox2, c-Myc) and culturing the cells at a 5% oxygen concentration for 1, 2 or 3 weeks from day 7 after the infection, or until day 40 after the infection, with those obtained at a normal oxygen concentration (20%). The results of three independent experiments are shown together.

Figure 10:
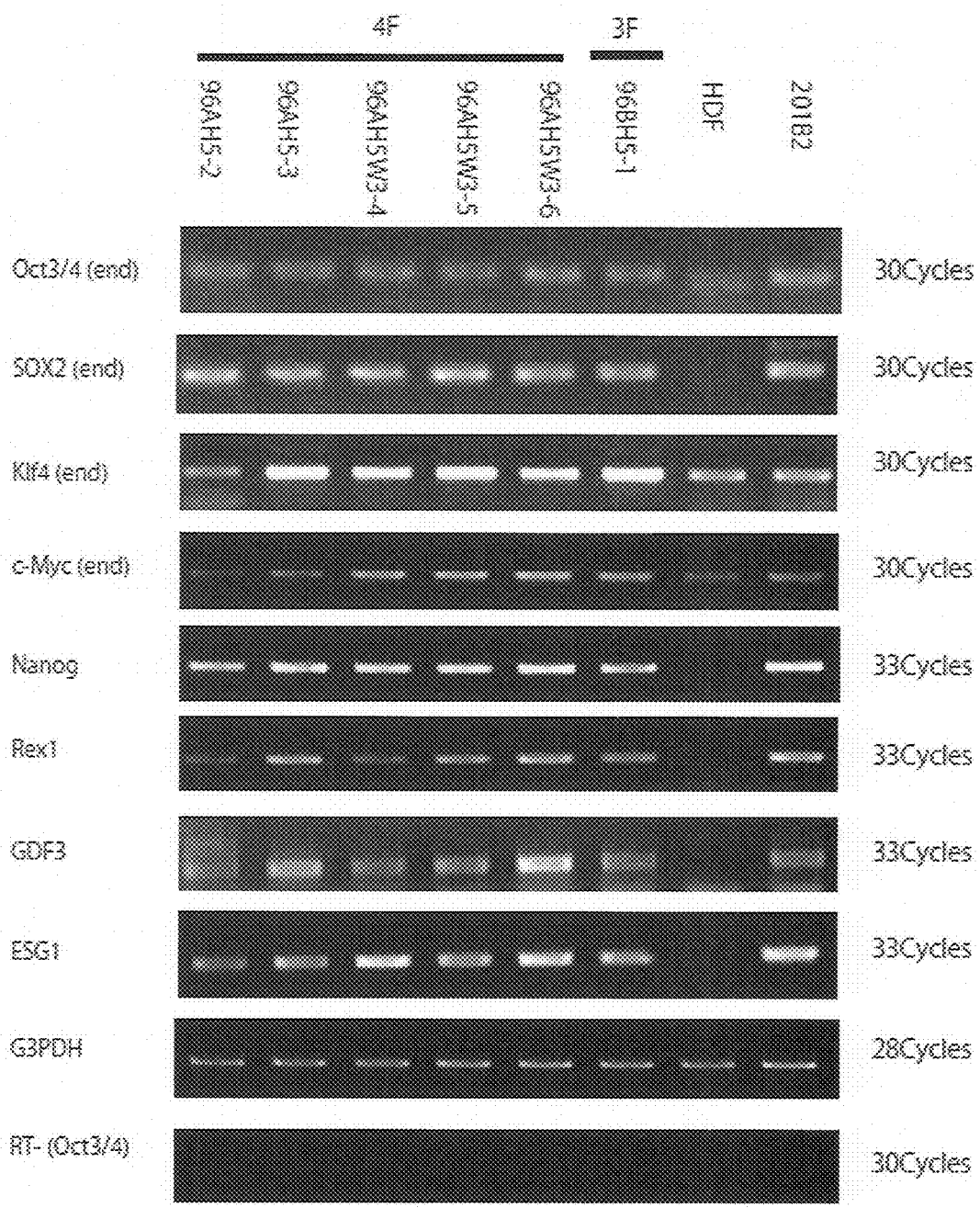

FIG. 10 is a photographic representation of results of RT-PCR performed using RNAs from iPS cells established at a low oxygen concentration. The expression of the markers for undifferentiated state Oct3/4(end), Sox2(end), Klf4(end), c-Myc(end), Nanog, Rex1, GDF1 and ESG1 was examined. The samples corresponding to the respective lanes are as follows:
96AH5-2 and 96AH5-3: 4 genes (Oct3/4, Klf4, Sox2, c-Myc) were introduced; cells were cultured at 5% oxygen concentration between day 7 and day 40 after infection
96AH5W3-4, 96AH5W3-5, 96AH5W3-6: 4 genes were introduced; cells were cultured at 5% oxygen concentration for 3 weeks starting on day 7 after the infection
96BH5-1: 3 genes (Oct3/4, Klf4, Sox2) were introduced; cells were pre-cultured at 5% oxygen concentration
201B2: Control iPS cells (Cell, 131, 861-872 (2007))
The numerical figure on the right side of each pannel indicates the number of PCR cycles.

Figure 11:
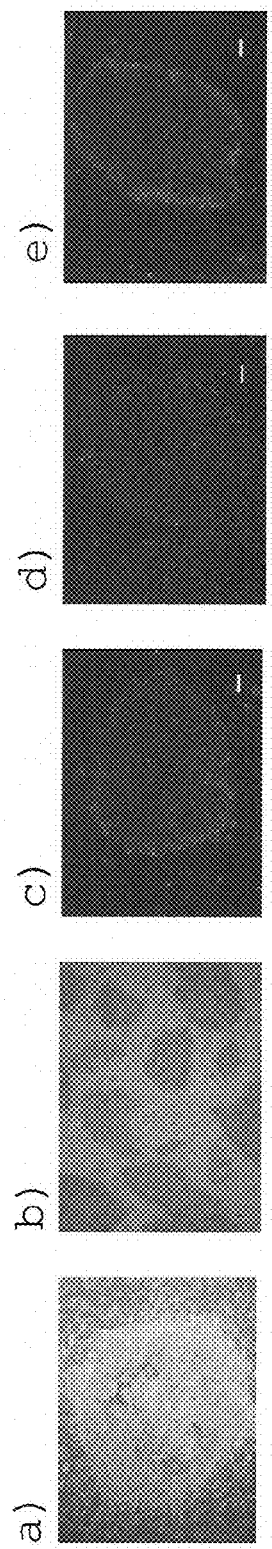

FIG. 11 shows a representative phase contrast image of human ES-like colonies (a) and alkaline phosphatase staining of the established iPS clone generated under 5% oxygen concentration (b). Immunohistochemical staining of undifferentiated human iPS cells generated under 5% oxygen concentration. Nanog (c), SSEA3 (d), SSEA4 (e).

Figure 12:
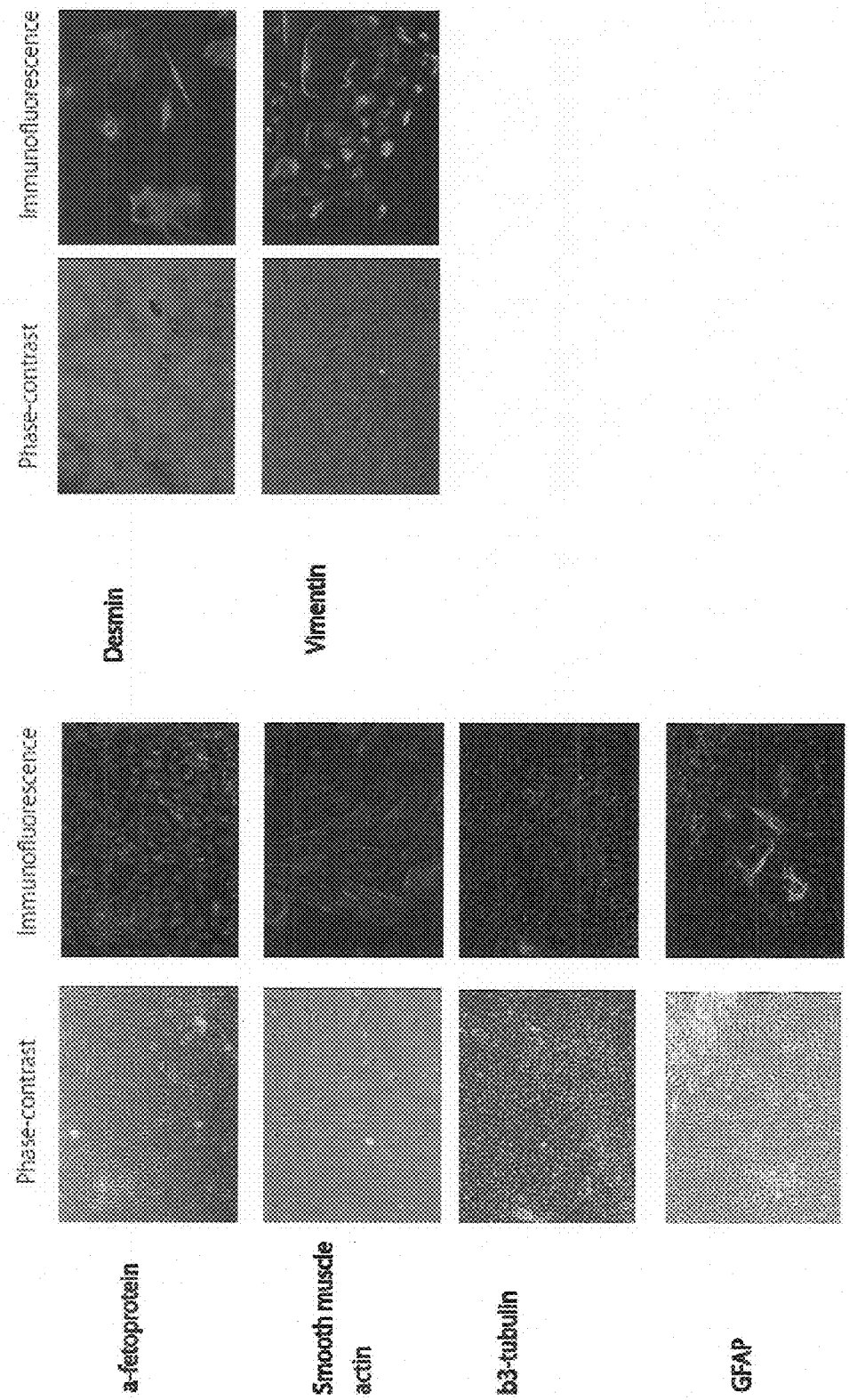

FIG. 12 is a photographic representation of results confirming that human iPS cells established by introducing four genes (Oct3/4, Klf4, Sox2, c-Myc) and culturing the starting cells at 5% oxygen concentration (70AH5-2, 70AH5-6) possess the potential for tridermic differentiation, obtained by staining with antibodies against α-fetoprotein, smooth muscle actin, βIII-tubulin, GFAP, Desmin and Vimentin [left: phase-contrast images; right: immunofluorescent images].

FIG. 13 shows histological staining images (hematoxylin-eosin staining) of teratomas obtained by injecting into the testis of an SCID mouse human iPS cells established by introducing four genes (Oct3/4, Klf4, Sox2, c-Myc) and culturing the starting cells at 5% oxygen concentration (70AH5-2) [a) nervous epithelial tissue, b) retinal epithelial tissue, c) osteoid tissue, d) smooth muscle tissue, e) endodermal epithelial tissue].

Figure 14:
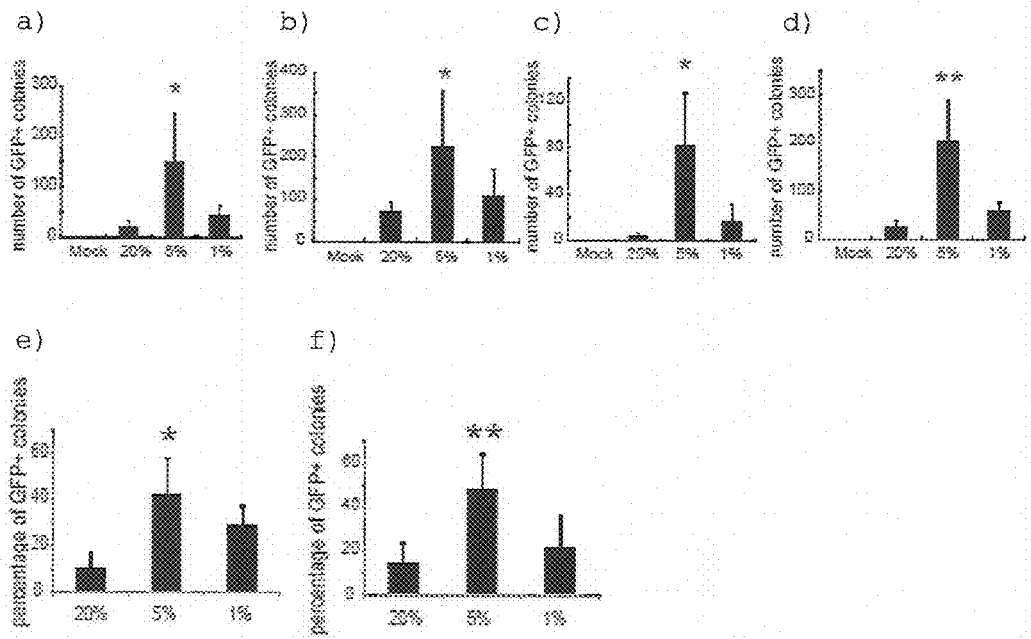

FIG. 14 (a) to (d) is a graphic representation comparing counts of the Nanog-GFP-positive colonies from four-factor transduced MEFs on day 21 (a) and on day 28 (b), from three-factor transduced MEFs on day 21 (c) and on day 28 (d). FIGS. 14 (e) and (f) is a graphic representation comparing the percentage of GFP-positive colonies in total colonies from to four-factor transduced MEFs (e) and three-factor transduced MEFs (f) on day 21.

Figure 15:
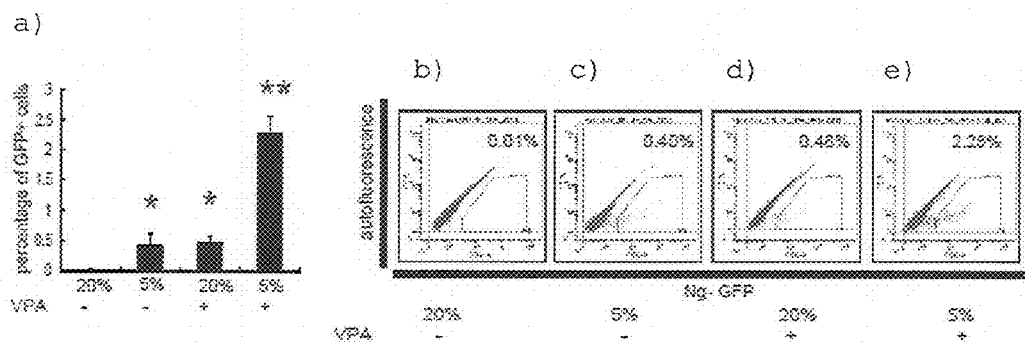

FIG. 15 (a) shows a graphic representation comparing percentage of GFP-positive cells from four-factor transduced MEFs on day 9 cultivated under hypoxic and normoxic conditions with and without valproic acid (VPA). FIG. 15 (b) to (e) show representative flow cytometric analysis of four-factor transduced MEFs under 20% oxygen (b) and 5% oxygen (c) without VPA, and under 20% oxygen (d) and under 5% oxygen (e) with VPA.

Figure 16:
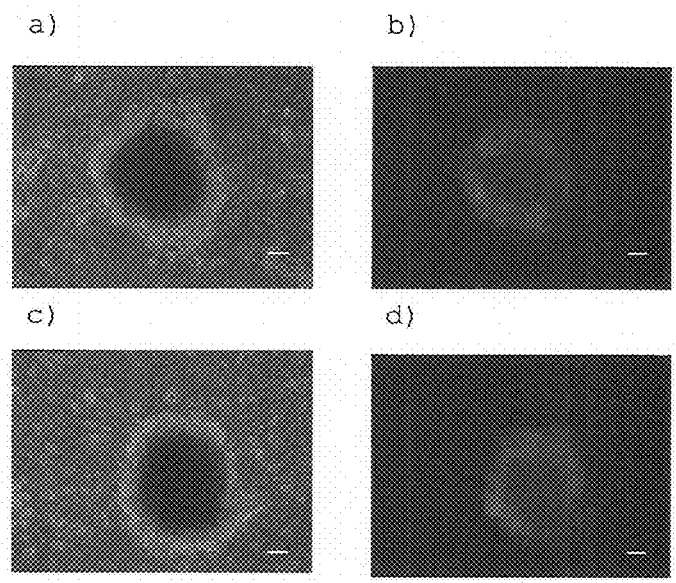

FIG. 16 shows the representative images of GFP-positive colonies under 20% oxygen ((a); phase contrast, (b); GFP) and 5% oxygen ((c); phase contrast, (d); GFP) on day 21 after transduction. Scale bars means 200 μm.

Figure 17:
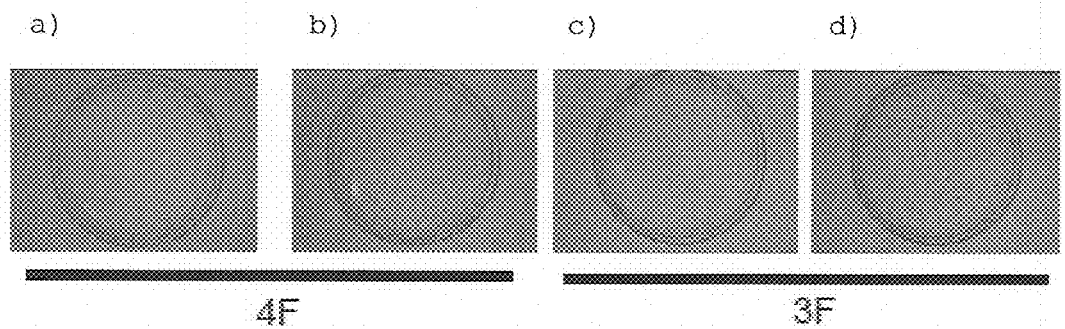

FIG. 17 shows the representative images of four-factor infected MEFs on day 21 under 20% oxygen (a) and 5% oxygen (b), three-factor infected MEFs on day 28 under 20% oxygen (c), and 5% oxygen (d).

FIG. 18 shows karyotype analysis of 527CH5-1.

FIG. 19 shows a graphic representation comparing percentage of apoptotic cells ES cells (RF8) (a) and four-factor transduced MEFs (b): ES cells were seeded onto the feeder layer of STO cells at the density of $1 \times 10^5$ cells/well and cultivated under normoxia or hypoxia from day 1 to 3. On day 3 the cells were treated with annexin V-FITC and subjected to flow cytometric analysis. Bar graphs represent the percentage of apoptotic cells (annexin V-FITC-positive). Four-factor transduced MEFs were seeded onto STO cells on day 4 posttransduction and cultivated under hypoxic and normoxic conditions from day 5 to day 9, and the cells were subjected to annexin-V affinity assay. Bar graphs represent the percentage of apoptotic cells. The averages and standard deviations of three experiments are shown.

Figure 20:
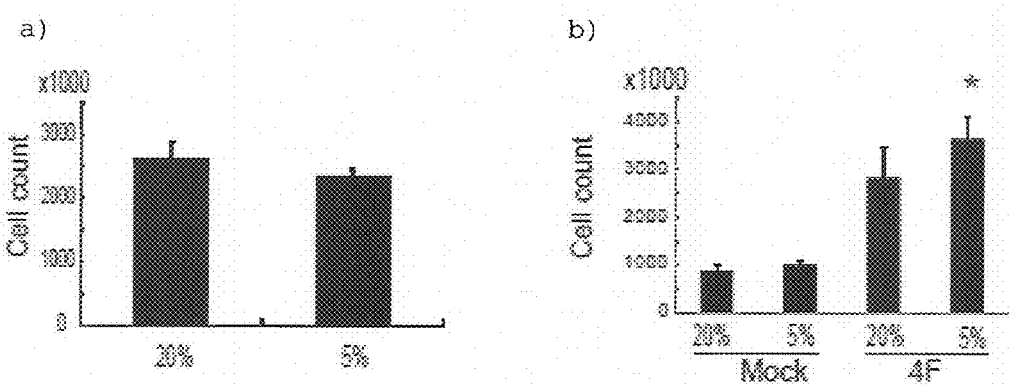

FIG. 20 shows a graphic representation comparing the cell number of ES cells (RF8) (a) and four-factor and mock transduced MEFs (b). The ES cells were seeded onto the feeder layer of STO cells at the density of $1 \times 10^5$ cells/well and cultivated under normoxia or hypoxia from day 1 to 3. On day 3, the number of the cells was counted. Bar graphs show the cell count of ES cells. The averages and standard deviations of three experiments are shown. Four-factor and mock transduced MEFs were cultivated respectively under hypoxic or normoxic conditions from day 1 to 4 and the number of cells were counted. Bar graphs show the cell count. The averages and standard deviations of four experiments are shown. * p>0.05

Figure 21:
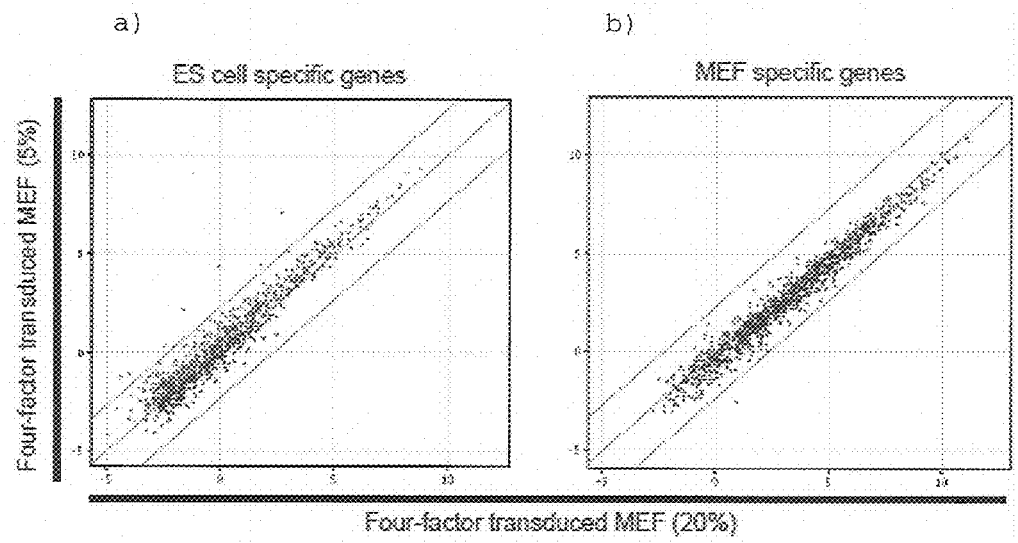

FIG. 21 shows scatter plots of expression patterns of ES cell-specific genes (a) and MEF-specific genes (b) comparing four-factor transduced MEFs under 5% oxygen with those under 20% oxygen. Genes that were specifically expressed in ES cells and MEFs were selected (more than tenfold difference). Up- and down-regulated genes in four-factor transduced MEFs with hypoxic treatment are shown in red and blue, respectively. Green lines indicate 5-fold changes in gene expression levels.

Figure 22:
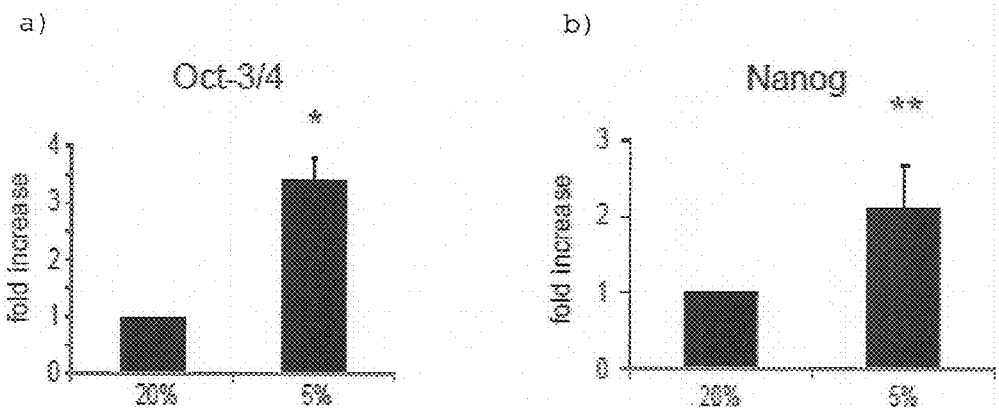

FIG. 22 shows the relative expression of endogenous Oct3/4 and Nanog by quantifying real-time RT-PCR.

Figure 23:
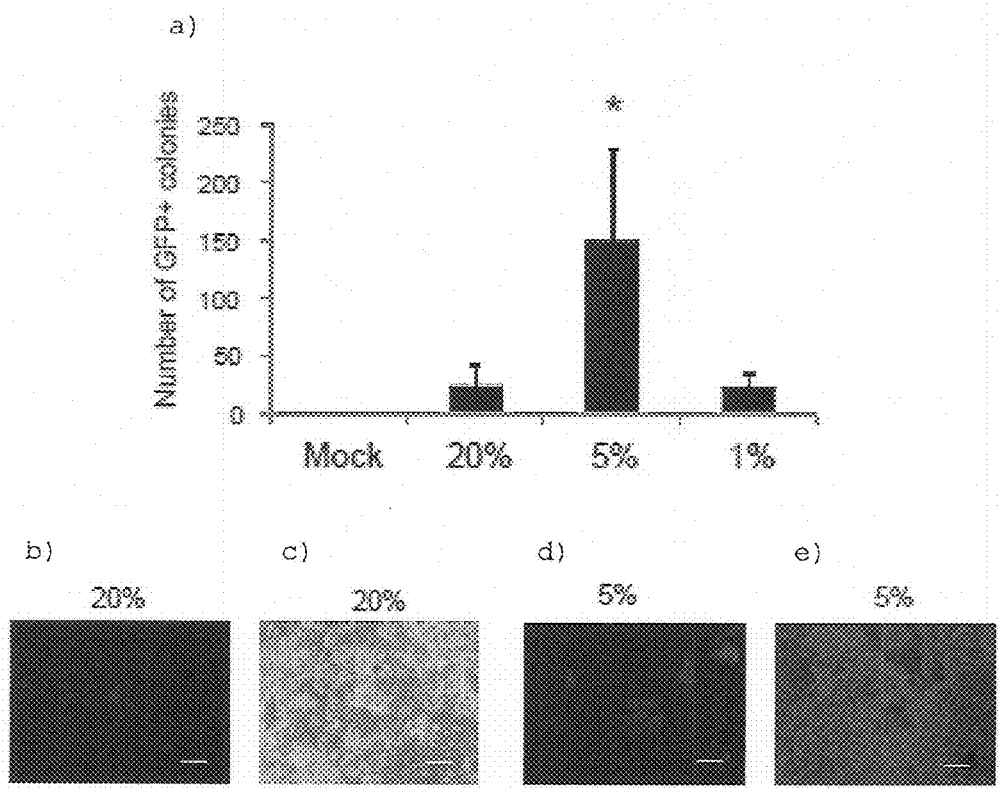

FIG. 23 (a) shows a graphic representation comparing the counts of the Nanog-GFP-positive colonies on day 21. The averages and standard deviations of three experiments are shown. Scale bars, 200 μm. * means p>0.05. FIG. 23 (b) to (e) show the representative image of GFP-positive colonies derived under 20% oxygen ((b); phase contrast, (c); GFP) and under 5% oxygen ((d); phase contrast, (e); GFP).

Figure 24:
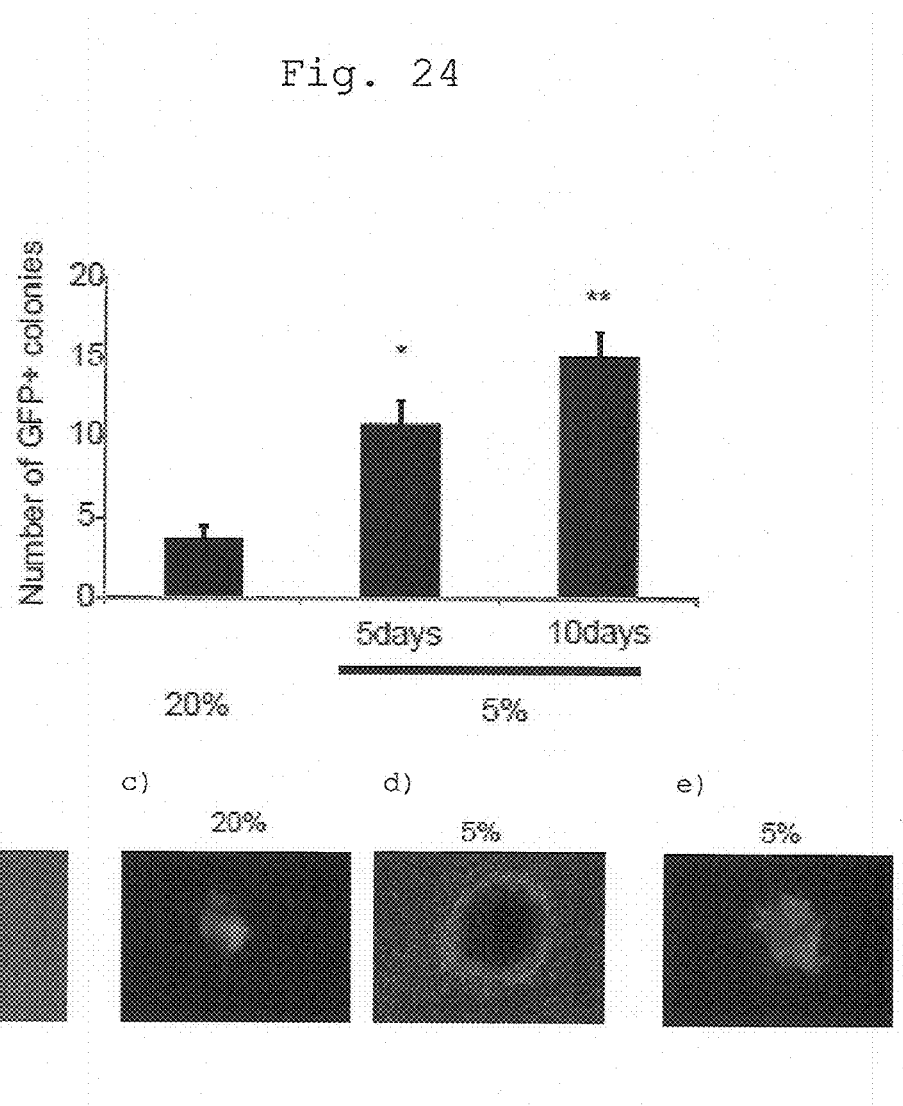

FIG. 24 (a) shows a graphic representation comparing each counts of the Nanog-GFP-positive colonies from reprogrammed MEFs by piggybac transposition on day 12. The averages and standard deviations of three experiments are shown. * and ** mean p<0.01 and p<0.001 respectively. FIG. 24 (b) to (e) show the representative image of GFP-positive colonies derived under 20% oxygen ((b); phase contrast, (c); GFP) and under 5% oxygen ((d); phase contrast, (e); GFP).

DETAILED DESCRIPTION OF THE INVENTION

The present invention provides a method of improving the efficiency of establishment of iPS cells, comprising culturing somatic cells under hypoxic conditions in the step of nuclear reprogramming thereof.

(a) Hypoxic Conditions

The term hypoxic conditions as used herein means that the oxygen concentration in the ambient atmosphere during cell culture is significantly lower than that in the air. Specifically, such conditions include lower oxygen concentrations than the oxygen concentrations in the ambient atmosphere of 5-10% $CO_2$/95-90% air, which is commonly used for ordinary cell culture; for example, oxygen concentrations of 18% or less in the ambient atmosphere are applicable. Preferably, the oxygen concentration in the ambient atmosphere is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The oxygen concentration in the ambient atmosphere is preferably 0.1% or more (e.g., 0.2% or more, 0.3% or more, 0.4% or more and the like), 0.5% or more (e.g., 0.6% or more, 0.7% or more, 0.8% or more, 0.9% or more and the like), or 1% or more (e.g., 1.1% or more, 1.2% or more, 1.3% or more, 1.4% or more and the like).

There is no limitation on how to create hypoxic conditions in a cellular environment; the easiest of suitable methods is to culture cells in a $CO_2$ incubator that allows control of oxygen concentrations. Such $CO_2$ incubators are commercially available from a number of manufacturers of equipment (e.g., $CO_2$ incubators for hypoxic culture manufactured by Thermo Scientific, Ikemoto Scientific Technology, Juji Field Inc., and Wakenyaku Co., Ltd. can be used).

The timing of beginning cell culture under hypoxic conditions is not particularly limited, as far as it does not interfere with improving the efficiency of establishment of iPS cells compared with that obtained at a normal oxygen concentration (20%). The starting time may be before or after contact of nuclear reprogramming substances with a somatic cell, and may be at the same time as the contact. For example, it is preferable that cell culture under hypoxic conditions be begun just after contacting a nuclear reprogramming substance with a somatic cell, or after a given time (e.g., 1 to 10 (e.g., 2, 3, 4, 5, 6, 7, 8 or 9) days) following the contact.

The duration of cell culture under hypoxic conditions is not particularly limited, as far as it does not interfere with improving the efficiency of establishment of iPS cells compared with that obtained at a normal oxygen concentration (20%); examples include, but are not limited to, between 3 days or more, 5 days or more, 7 days or more or 10 days or more, and 50 days or less, 40 days or less, 35 days or less or 30 days or less. The preferred duration of cell culture under hypoxic conditions also varies depending on the oxygen concentration in the ambient atmosphere; those skilled in the art can adjust as appropriate the duration of cell culture according to the oxygen concentration used. For example, the preferred duration is decided by comparing ES cell specific genes expression in the reprogrammed cells on the low oxygen condition with on the nomal oxygen condition. In an embodiment of the present invention, when iPS cell candidate colonies are selected with drug resistance as an indicator, it is preferable that a normal oxygen concentration be restored from hypoxic conditions by the start of drug selection.

Furthermore, the preferred starting time and duration of cell culture under hypoxic conditions also vary depending on the choice of nuclear reprogramming substances used, the efficiency of establishment of iPS cells under conditions involving a normal oxygen concentration, and other factors. For example, when the three factors Oct3/4, Klf4, and Sox2 are introduced into a human somatic cell, it is preferable that the cell be cultured under hypoxic conditions for 3 to 10 (e.g., 4, 5, 6, 7, 8, 9) days starting relatively early after contact with nuclear reprogramming substances (e.g., after 0 to 3 (e.g., 1, 2) days).

(b) Sources of Somatic Cells

Any cells, but other than germ cells, of mammalian origin (e.g., mice, humans) can be used as starting material for the production of iPS cells in the present invention. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as nerve stem cells, hematopoietic stem cells, mesenchymal stem cells, and dental pulp stem cells.

The choice of mammal as a source of somatic cells is not particularly limited; however, when the iPS cells obtained are to be used for regenerative medicine in humans, it is particularly preferable, from the viewpoint of prevention of graft rejection, that somatic cells are patient's own cells or collected from another person (donor) having the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressor and the like. For example, substantially the same HLA type includes an HLA type wherein the three major HLAs HLA-A, HLA-B and HLA-DR are identical to a recipient (hereinafter the same meaning shall apply). When the iPS cells obtained are not to be administered (transplanted) to a human, but used as, for example, a source of cells for screening for evaluating a patient's drug susceptibility or adverse reactions, it is likewise necessary to collect the somatic cells from the patient or another person with the same genetic polymorphism correlating with the drug susceptibility or adverse reactions.

(c) Nuclear Reprogramming Substances

In the present invention, "a nuclear reprogramming substance" refers to any substance(s) capable of inducing an iPs cell from a somatic cell, which may be composed of any substance such as a proteinous factor or a nucleic acid that encodes the same (including forms incorporated in a vector), or a low-molecular compound. When the nuclear reprogramming substance is a proteinous factor or a nucleic acid that encodes the same, the following combinations, for example, are preferable (hereinafter, only the names for proteinous factors are shown).

(1) Oct3/4, Klf4, c-Myc
(2) Oct3/4, Klf4, c-Myc, Sox2 (Sox2 is replaceable with Sox1, Sox3, Sox15, Sox17 or Sox18; Klf4 is replaceable with Klf1, Klf2 or Klf5; c-Myc is replaceable with T58A (active mutant), N-Myc, or L-Myc)
(3) Oct3/4, Klf4, c-Myc, Sox2, Fbx15, Nanog, Eras, ECAT15-2, TclI, β-catenin (active mutant S33Y)
(4) Oct3/4, Klf4, c-Myc, Sox2, TERT, SV40 Large T
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmi1
[For more information on the factors shown above, see WO 2007/069666 (for information on replacement of Sox2 with Sox18 and replacement of Klf4 with Klf1 or Klf5 in the combination (2) above, see *Nature Biotechnology*, 26, 101-106 (2008)); for the combination "Oct3/4, Klf4, c-Myc, Sox2", see also *Cell*, 126, 663-676 (2006), *Cell*, 131, 861-872 (2007) and the like; for the combination "Oct3/4, Klf4, c-Myc, Sox2, hTERT, SV40 Large T", see also *Nature*, 451, 141-146 (2008).]
(9) Oct3/4, Klf4, Sox2 [see *Nature Biotechnology*, 26, 101-106 (2008)]
(10) Oct3/4, Sox2, Nanog, Lin28 [see *Science*, 318, 1917-1920 (2007)]

(11) Oct3/4, Sox2, Nanog, Lin28, hTERT, SV40 Large T (see *Stem Cells*, 26, 1998-2005 (2008))
(12) Oct3/4, Klf4, c-Myc, Sox2, Nanog, Lin28 [see *Cell Research* (2008) 600-603]
(13) Oct3/4, Klf4, c-Myc, Sox2, SV40 Large T (see also *Stem Cells*, 26, 1998-2005 (2008))
(14) Oct3/4, Klf4 [see also *Nature*, 454, 646-650 (2008); *Cell Stem Cell*, 2: 525-528 (2008)]
(15) Oct3/4, c-Myc [see *Nature*, 454, 646-650 (2008)]
(16) Oct3/4, Sox2 [see *Nature*, 451, 141-146 (2008), WO2008/118820]
(17) Oct3/4, Sox2, Nanog (see WO2008/118820)
(18) Oct3/4, Sox2, Lin28 (see WO2008/118820)
(19) Oct3/4, Sox2, c-Myc, Esrrb (here, Esrrb is replaceable with Esrrg; see *Nat. Cell Biol.*, 11, 197-203 (2009))
(20) Oct3/4, Sox2, Esrrb (see *Nat. Cell Biol.*, 11, 197-203 (2009))
(21) Oct3/4, Klf4, L-Myc
(22) Oct3/4, Nanog
(23) Oct3/4
(24) Oct3/4, Klf4, c-Myc, Sox2, Nanog, Lin28, SV40LT (see *Science*, 324: 797-801 (2009))

In (1)-(24) above, in place of Oct3/4, other members of the Oct family, for example, Oct1A, Oct6 and the like, can also be used. In place of Sox2 (or Sox1, Sox3, Sox15, Sox17, Sox18), other members of the Sox family, for example, Sox7 and the like, can also be used. In place of c-Myc, other members of the Myc family, for example, L-Myc and the like, can also be used. In place of Lin28, other members of the Lin family, for example, Lin28b and the like, can also be used.

Any combination that does not fall in (1) to (24) above but comprises all the constituents of any one of (1) to (24) above and further comprises an optionally chosen other substance can also be included in the scope of "nuclear reprogramming substances" in the present invention. Provided that the somatic cell to undergo nuclear reprogramming is endogenously expressing one or more of the constituents of any one of (1) to (24) above at a level sufficient to cause nuclear reprogramming, a combination of only the remaining constituents excluding the one or more constituents can also be included in the scope of "nuclear reprogramming substances" in the present invention.

Among these combinations, as examples of preferable nuclear reprogramming substances, at least one, preferably two or more, more preferably 3 or more selected from Oct3/4, Sox2, Klf4, c-Myc, Nanog, Lin28 and SV40 Large T can be mentioned.

If the iPS cells obtained are to be used for therapeutic purposes, the three factors Oct3/4, Sox2 and Klf4 [combination (9) above] are preferably used. If the iPS cells obtained are not to be used for therapeutic purposes (e.g., used as an investigational tool for drug discovery screening and the like), the five factors Oct3/4, Klf4, c-Myc, Sox2 and Lin28, or the six factors consisting of the five factors and Nanog [combination (12) above] are preferable. In these preferred combinations, L-Myc can also be used in place of c-Myc.

Information on the mouse and human cDNA sequences of the aforementioned proteinous factors is available with reference to the NCBI accession numbers mentioned in WO 2007/069666 (in the publication, Nanog is described as ECAT4). Mouse and human cDNA sequence information on Lin28, Lin28b, Esrrb, and Esrrg can be acquired by referring to the following NCBI accession numbers, respectively); those skilled in the art are easily able to isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when the nuclear reprogramming substance used is a nucleic acid that encodes a proteinous factor, the cDNA obtained is inserted into a viral or plasmid vector to construct an expression vector, and the vector is subjected to the step of nuclear reprogramming.

Contact of nuclear reprogramming substance(s) with a somatic cell can be achieved using a method known per se for protein transfer into cells when the substance is a proteinous factor. Such methods include, for example, the method using a protein transfer reagent, the method using a protein transfer domain (PTD)—or cell penetrating peptide (CPP)—fusion protein, the microinjection method and the like. Protein transfer reagents are commercially available, including those based on a cationic lipid, such as BioPOTER Protein Delivery Reagent (Genlantis), Pro-Ject™ Protein Transfection Reagent (PIERCE), PULSin™ delivery reagent (Polyplus-transfection) and ProVectin (IMGENEX); those based on a lipid, such as Profect-1 (Targeting Systems); those based on a membrane-permeable peptide, such as Penetrain Peptide (Q biogene) and Chariot Kit (Active Motif), and the like. The transfer can be achieved per the protocols attached to these reagents, a common procedure being as described below. Nuclear reprogramming substance(s) is(are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium. Specific means using the protein transfer reagent is disclosed in WO 2009/073523 or WO 2009/032456.

Developed PTDs include those using transcellular domains of proteins such as drosophila-derived AntP, HIV-derived TAT (Frankel, A. et al, *Cell* 55, 1189-93 (1988) or Green, M. & Loewenstein, P. M. *Cell* 55, 1179-88 (1988)), Penetratin (Derossi, D. et al, *J. Biol. Chem.* 269, 10444-50 (1994)), Buforin II (Park, C. B. et al. *Proc. Natl. Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell*, 4, 381-384 (2009)) and 9R (*Cell Stem Cell*, 4, 472-476 (2009)). A fusion protein expression vector incorporating a cDNA of a nuclear reprogramming substance and a PTD or CPP sequence is prepared to allow the recombinant expression of the fusion protein, and the fusion protein is recovered for use in for transfer. This transfer can be achieved as described above, except that no protein transfer reagent is added. Specific means using the CPP is disclosed in Cell Stem Cell, 4:472-6 (2009) or Cell Stem Cell, 4:381-4 (2009).

Microinjection, a method of placing a protein solution in a glass needle having a tip diameter of about 1 μm, and injecting the solution into a cell, ensures the transfer of the protein into the cell.

A sustained overexpression of a nuclear reprogramming gene potentially increases the risk of carcinogenesis; however, because a proteinous reprogramming factor undergoes degradation by protease in the transfected cell and disappears gradually, use of the proteinous factor can be suitable in cases where high safety is required as in the case where the iPS cells obtained are utilized for therapeutic purposes.

However, taking into account the ease of transfer into a somatic cell, nuclear reprogramming substance may also be used preferably in the form of a nucleic acid that encodes a proteinous factor, rather than the factor as it is. The nucleic acid may be a DNA or an RNA, or a DNA/RNA chimera, and may be double-stranded or single-stranded. Preferably, the nucleic acid is a double-stranded DNA, particularly a cDNA.

A cDNA of a nuclear reprogramming substance is inserted into an appropriate expression vector comprising a promoter capable of functioning in a host somatic cell. Useful expression vectors include, for example, viral vectors such as retrovirus, lentivirus, adenovirus, adeno-associated virus, herpesvirus and Sendai virus, plasmids for the expression in animal cells (e.g., pA1-11, pXT1, pRc/CMV, pRc/RSV, pcDNAI/Neo) and the like. A kind of vector used can be chosen as appropriate according to the intended use of the iPS cells obtained.

Examples of promoters used in expression vectors include the EF-alpha promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF-alpha promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of useful selectable marker genes include the dihydrofolate reductase gene, the neomycin resistant gene, the puromycin resistant gene and the like.

When two or more nucleic acids are introduced into a cell as nuclear reprogramming substances, the nucleic acids may be carried by separate vectors, and a plurality of nucleic acids may be joined tandem to obtain a polycistronic vector. In the latter case, to enable efficient polycistronic expression, it is desirable that the 2A self-cleaving peptide of foot-and-mouth disease virus (see *Science,* 322, 949-953, 2008 and the like), IRES sequence and the like, preferably the 2A sequence be ligated between the individual nucleic acids.

An expression vector harboring a nucleic acid as a nuclear reprogramming substance can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. For example, specific means using a retroviral vector are disclosed in WO2007/69666, *Cell,* 126, 663-676 (2006) and *Cell,* 131, 861-872 (2007). Specific means using a lentivirus vector is disclosed in *Science,* 318, 1917-1920 (2007). Specific means using an adenoviral vector is disclosed in *Science,* 322, 945-949 (2008).

As discussed above, when iPS cells are utilized for therapeutic purposes, a sustained overexpression of a nuclear reprogramming gene potentially increases the risk of carcinogenesis in tissues and organs differentiated from iPS cells; therefore, a nucleic acid as a nuclear reprogramming substance is preferably expressed transiently, without being integrated into the chromosome of the cells. From this viewpoint, use of an adenoviral vector, whose integration into chromosome is rare, is preferred. Specific means using an adenoviral vector is disclosed in *Science,* 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.,* 282, 27383-27391 (2007) and JP-3602058 B can be used.

When a retroviral vector or a lentiviral vector is used, even if silencing of the transgene has occurred, it possibly becomes reactivated; therefore, for example, a method can be used preferably wherein a nucleic acid as a nuclear reprogramming substance is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivated (SIN) LTR prepared by deleting the sequence, or substituting the sequence with a polyadenylation sequence such as of SV40. Specific means using the Cre-loxP system and SIN LTR is disclosed in Chang et al., *Stem Cells,* 27: 1042-1049 (2009).

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Also when a plasmid vector is used, its integration into chromosome is rare, the transgene is degraded and removed by DNase in the cells; therefore, when iPS cells are utilized for therapeutic purposes, use of a plasmid vector can be another preferred mode of embodiment. Specific means using a plasmid as a vector are described in, for example, *Science,* 322, 949-953 (2008) and the like.

Another preferable non-integration type vector is an episomal vector, which is autonomously replicable outside chromosome. Specific means using an episomal vector is disclosed in *Science*, 324, 797-801 (2009).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009)☐ Woltjen et al., *Nature*, 458: 766-770 (2009). In another embodiment, tetracycline responsive element in promoter region ( Tet-On® & Tet-Off® Gene Expression Systems, Clontech) can be used for the excision of transgenes.

The number of repeats of the manipulation to introduce an adenoviral or non-viral expression vector into a somatic cell is not particularly limited, the transfection can be performed once or more optionally chosen times (e.g., once to 10 times, once to 5 times or the like). When two or more kinds of adenoviral or non-viral expression vectors are introduced into a somatic cell, it is preferable that these all kinds of adenoviral or non-viral expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

When the nuclear reprogramming substance is a low-molecular compound, contact thereof with a somatic cell can be achieved by dissolving the substance at an appropriate concentration in an aqueous or non-aqueous solvent, adding the solution to a medium suitable for cultivation of somatic cells isolated from a mammal such as human or mouse [e.g., minimal essential medium (MEM) comprising about 5 to 20% fetal bovine serum, Dulbecco's modified Eagle medium (DMEM), RPMI1640 medium, 199 medium, F12 medium and combinations thereof, and the like] so that the nuclear reprogramming substance concentration will fall in a range that is sufficient to cause nuclear reprogramming in somatic cells and does not cause cytotoxicity, and culturing the cells for a given period. The nuclear reprogramming substance concentration varies depending on the kind of nuclear reprogramming substance used, and is chosen as appropriate over the range of about 0.1 nM to about 100 nM. Duration of contact is not particularly limited, as far as it is sufficient to cause nuclear reprogramming of the cells; usually, the nuclear reprogramming substance may be allowed to be co-present in the medium until a positive colony emerges.

(d) iPS Cell Establishment Efficiency Improvers

In recent years, various substances that improve the efficiency of establishment of iPS cells, which has traditionally been low, have been proposed one after another. When brought into contact with a somatic cell together with the aforementioned nuclear reprogramming substances, these establishment efficiency improvers are expected to further raise the efficiency of establishment of iPS cells.

Examples of iPS cell establishment efficiency improvers include, but are not limited to, histone deacetylase (HDAC) inhibitors [e.g., valproic acid (VPA) (*Nat. Biotechnol.*, 26(7): 795-797 (2008)], low-molecular inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine) [*Nat. Biotechnol.*, 26(7): 795-797 (2008)], G9a histone methyltransferase inhibitors [e.g., low-molecular inhibitors such as BIX-01294 (*Cell Stem Cell*, 2: 525-528 (2008)], nucleic acid-based expression inhibitors such as siRNAs and shRNAs against G9a [e.g., G9a siRNA (human) (Santa Cruz Biotechnology) and the like) and the like], L-channel calcium agonists (e.g., Bayk8644) [*Cell Stem Cell*, 3, 568-574 (2008)], p53 inhibitors [e.g., siRNA and shRNA against p53 (*Cell Stem Cell*, 3, 475-479 (2008)), UTF1 *[Cell Stem Cell*, 3, 475-479 (2008)], Wnt Signaling inducers (e.g., soluble Wnt3a) [*Cell Stem Cell*, 3, 132-135 (2008)], 2i/LIF [21 is an inhibitor of mitogen-activated protein kinase signaling and glycogen synthase kinase-3, *PloS Biology*, 6(10), 2237-2247 (2008)] and the like. As mentioned above, the nucleic acid-based expression inhibitors may be in the form of expression vectors harboring a DNA that encodes an siRNA or shRNA.

Among the constituents of the aforementioned nuclear reprogramming substances, SV40 large T and the like, for example, can also be included in the scope of iPS cell establishment efficiency improvers because they are deemed not essential, but auxiliary, factors for somatic cell nuclear reprogramming. In the situation of the mechanisms for nuclear reprogramming remaining unclear, the auxiliary factors, which are not essential for nuclear reprogramming, may be conveniently considered as nuclear reprogramming substances or iPS cell establishment efficiency improvers. Hence, because the somatic cell nuclear reprogramming process is understood as an overall event resulting from contact of nuclear reprogramming substance(s) and iPS cell establishment efficiency Improver(s) with a somatic cell, it seems unnecessary for those skilled in the art to always distinguish between the nuclear reprogramming substance and the iPS cell establishment efficiency improver.

Contact of an iPS cell establishment efficiency improver with a somatic cell can be achieved as described above for each of three cases: (a) the improver is a proteinous factor, (b) the improver is a nucleic acid that encodes the proteinous factor, and (c) the improver is a low-molecular compound.

An iPS cell establishment efficiency improver may be brought into contact with a somatic cell simultaneously with a nuclear reprogramming substance, or either one may be contacted in advance, as far as the efficiency of establishment of iPS cells from the somatic cell is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming substance and an iPS cell establishment efficiency improver are both used in the form of a viral or non-viral vector, for example, both may be simultaneously introduced into the cell.

Somatic cells separated from a mammal such as mouse or human can be pre-cultured using a medium known per se suitable for the cultivation thereof, depending on the kind of the cells. Examples of such media include, but are not limited to, a minimal essential medium (MEM) containing about 5 to 20% fetal calf serum, Dulbecco's modified Eagle medium (DMEM), RPMI1640 medium, 199 medium, F12 medium and combinations thereof, and the like. Reports are available that by conducting pre-culture at a low serum concentration of 5% or less, the efficiency of establishment of iPS cells was improved (for example, WO 2009/006997). When using, for example, a transfection reagent such as a cationic liposome in contacting the cell with nuclear reprogramming substance(s) and iPS cell establishment efficiency improver(s), it is sometimes preferable that the medium be previously replaced with a serum-free medium to prevent a reduction in the transfer efficiency. After the nuclear reprogramming substance(s) (and iPS cell establishment efficiency improver(s)) is(are) brought into contact with the cell, the cell can be cultured under conditions suitable for the cultivation of, for example, ES cells. In the case of mouse cells, the cultivation is carried out with the addition of Leukemia Inhibitory Factor (LIF) as a differentiation suppressor to an ordinary medium. Meanwhile, in the case of human cells, it is desirable that basic fibroblast growth factor (bFGF) and/or stem cell factor (SCF) be added in place of LIF. Usually, the cells are cultured in the co-presence of mouse embryo-derived fibroblasts (MEFs) treated with radiation or an antibiotic to terminate the cell division thereof, as feeder cells. Usually, STO cells and the like are commonly used as MEFs, but for inducing iPS cells, SNL cells [McMahon, A. P. & Bradley, A. Cell 62, 1073-1085 (1990)] and the like are commonly used. Co-culture with feeder cells may be started before contact of the nuclear reprogramming substance, at the time of the contact, or after the contact (e.g., 1-10 days later).

A candidate colony of iPS cells can be selected by a method with drug resistance and reporter activity as indicators, and also by a method based on visual examination of morphology. As an example of the former, a colony positive for drug resistance and/or reporter activity is selected using a recombinant somatic cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant somatic cells include MEFs from a mouse having the βgeo (which encodes a fusion protein of β-galactosidase and neomycin phosphotransferase) gene knocked-in to the Fbx15 locus [Takahashi & Yamanaka, Cell, 126, 663-676 (2006)], MEFs from a transgenic mouse having the green fluorescent protein (GFP) gene and the puromycin resistance gene integrated in the Nanog locus [Okita et al., Nature, 448, 313-317 (2007)] and the like. Meanwhile, examples of the latter method based on visual examination of morphology include the method described by Takahashi et al. in Cell, 131, 861-872 (2007). Although the method using reporter cells is convenient and efficient, it is desirable from the viewpoint of safety that colonies be selected by visual examination when iPS cells are prepared for the purpose of human treatment. When the three factors Oct3/4, Klf4 and Sox2 are used as nuclear reprogramming substances, the number of clones established decreases but the resulting colonies are mostly of iPS cells of high quality comparable to ES cells, so that iPS cells can efficiently be established even without using reporter cells.

The identity of the cells of a selected colony as iPS cells can be confirmed by positive responses to a Nanog (or Oct3/4, Fbx15) reporter (GFP positivity, β-galactosidase positivity and the like) and positive responses to selection markers (puromycin resistance, G418 resistance and the like), as well as by the formation of a visible ES cell-like colony, as described above. However, to ensure higher accuracy, it is possible to perform tests such as analyzing the expression of various ES-cell-specific genes and transplanting the cells selected to a mouse and confirming the formation of teratomas.

The iPS cells thus established can be used for various purposes. For example, by utilizing a reported method of differentiation induction for ES cells, differentiation of the iPS cells into various cells (e.g., myocardial cells, blood cells, nerve cells, vascular endothelial cells, insulin-secreting cells and the like) can be induced. Therefore, inducing iPS cells using somatic cells collected from a patient would enable stem cell therapy based on autologous transplantation, wherein the iPS cells are differentiated into desired cells (cells of an affected organ of the patient, cells that have a therapeutic effect on disease, and the like), and the differentiated cells are transplanted to the patient. Somatic cells collected not from a patient, but from another person with the same or substantially the same HLA type as that of the patient, may be used to induce iPS cells, which are differentiated into desired cells for use in transplantation to the patient. Furthermore, because functional cells (e.g., liver cells) differentiated from iPS cells are thought to is better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Example 1

Effect (1) of the Hypoxic Culture Method on the Establishment of iPS Cells

Mice having a Nanog reporter were used as an experimental system. The Nanog reporter used was prepared by inserting the enhanced green fluorescent protein (EGFP) and puromycin resistant genes into the Nanog locus of a BAC (bacterial artificial chromosome) purchased from BACPAC Resources [Okita K. et al., Nature 448, 313-317 (2007)]. The mouse Nanog gene is expressed specifically in pluripotent cells such as ES cells and early embryos. The mouse iPS cells that have become positive for this reporter are known to be nearly equivalent to ES cells in terms of differentiation potential. Mouse embryonic fibroblasts (MEFs) and tail-tip fibroblasts (TTFs) obtained from a Nanog reporter mouse having this Nanog reporter [Okita K. et al., Nature 448, 313-317 (2007)] were transfected by means of retroviruses to establish iPS cells, and colonies expressing EGFP from the Nanog reporter were counted to evaluate the efficiency of establishment of iPS cells.

The retroviruses used for reprogramming were prepared by introducing each retroviral expression vector [pMXs-Oct3/4, pMXs-Sox2, pMXs-Klf4, pMXs-cMyc: Cell, 126, 663-676 (2006)] into Plat-E cells (Morita, S. et al., *Gene Ther.* 7, 1063-1066) sown at $2\times10^6$ cells per 100 mm culture dish (Falcon) on the previous day. The culture medium used was DMEM/10% FCS [DMEM (Nacalai Tesque) supplemented with 10% fetal bovine serum], and the cells were cultured at 37° C. in the presence of 5% $CO_2$. For vector introduction, 27 μL of the FuGene6 transfection reagent (Roche) was placed in 300 μl of Opti-MEM I Reduced-Serum Medium (Invitrogen), and the medium was allowed to stand at room temperature for 5 minutes. Thereafter, 9 μg of each expression vector was added, and the medium was allowed to stand at room temperature for 15 minutes, and then added to the Plat-E culture broth. On day 2, the Plat-E culture supernatant was replaced with a fresh medium. On day 3, the culture supernatant was recovered and filtered through a 0.45 μm sterile filter (Whatman), polybrene (Nacalai Tesque) was added to obtain a concentration of 4 μg/mL, and this was used as the viral fluid.

Mouse embryonic fibroblasts (MEFs) were isolated from a fetus at 13.5 days after fertilization of a Nanog reporter mouse, and cultured with a medium (DMEM/10% FCS). The tail-tip fibroblasts (TTFs) used were obtained by shredding the tail-tip of a Nanog reporter mouse, placing the pieces of the tissue standing on a gelatin-coated 6-well dish, culturing them in a primary culture cell starting medium (Toyobo Life Science Department) for 5 days, and further culturing the fibroblasts migrating from the tail-tip tissue onto the dish with the DMEM/10% FCS medium.

Not expressing the Nanog gene, MEFs and TTFs do not express EGFP and do not emit green fluorescence. Not expressing the puromycin resistance gene as well, MEFs and TTFs are susceptible to the antibiotic puromycin. As such, MEFs and TTFs were sown to a 6-well culture plate (Falcon) coated with 0.1% gelatin (Sigma) at $1\times10^5$ cells per well. The culture medium used was DMEM/10% FCS, and the cells were cultured at 37° C. and 5% $CO_2$. The following day, each retroviral fluid was added to introduce genes by overnight infection.

Starting on day 3 after the viral infection, the cells were cultured using an LIF-supplemented ES cell culture medium [prepared by adding to DMEM (Nacalai Tesque) 15% fetal bovine serum, 2 mM L-glutamine (Invitrogen), 100 μM non-essential amino acids (Invitrogen), 100 μM 2-mercaptoethanol (Invitrogen), 50 U/mL penicillin (Invitrogen) and 50 mg/mL streptomycin (Invitrogen)]. On day 4 after the infection, the media for the MEFs and TTFs were removed, and the cells were washed by the addition of 1 mL of PBS. After the PBS was removed, 0.25% trypsin/1 mM EDTA (Invitrogen) was added, and a reaction was allowed to proceed at 37° C. for about 5 minutes. After the cells floated up, they were suspended by the addition of the ES cell culture medium; $1\times10^4$ MEF cells (when the four factors Oct3/4, Sox2, Klf4 and c-Myc were introduced) or $1\times10^5$ MEF cells (when the three factors Oct3/4, Sox2 and Klf4 were introduced) were sown to a 100-mm dish having feeder cells sown thereto previously. For the TTF cells, $2\times10^4$ TTF cells (when the aforementioned four factors were introduced), $1\times10^5$ TTF cells (when the aforementioned three factors were introduced), or $1.5\times10^5$ TTF cells (when the three factors Oct3/4, Klf4 and c-Myc were introduced) were sown in the same manner. The feeder cells used were SNL cells treated with mitomycin C to terminate the cell division thereof [McMahon, A. P. & Bradley, A. *Cell* 62, 1073-1085 (1990)]. Subsequently, the ES cell culture medium was exchanged with a fresh supply every two days until a colony became observable.

Between days 5 and 14 after the infection, the cells were cultured in an incubator (Thermo Scientific) set at a normal oxygen concentration (20%) or low oxygen concentrations (5%, 1%). Selection with puromycin (1.5 μg/mL) was started on day 14 for the cells infected with four factors (Oct3/4, Sox2, Klf4, c-Myc), and on day 21 for the cells infected with three factors (Oct3/4, Sox2, Klf4 or Oct3/4, Klf4, c-Myc). Colonies emerged about on day 10 for the four factors, and about on day 20 for the three factors, and became GFP-positive gradually.

On days 21 and 28 after the infection, GFP-positive colonies were counted; comparisons were made between the cells cultured at a normal oxygen concentration (20%) and those cultured at low oxygen concentrations (5%, 1%). The results for the MEFs are shown in Table 1; the results for the TTFs are shown in Tables 2 and 3. These results demonstrate that the efficiency of establishment of iPS cells increases with cell culture under hypoxic conditions. In particular, when the oxygen concentration was 5%, good results were obtained (Tables 1-3). In case of introduction of three factors, it was found that iPS cells could be established not only with Oct3/4, Sox2, and Klf4, but also with Oct3/4, Klf4, and c-Myc (Table 2).

TABLE 1

| c-Myc (mL) | Oct3/4 (mL) | Sox2 (mL) | Klf4 (mL) | mock (mL) | Number of cells resown | Oxygen concentration (%) | 21 days after infection puro$^r$ | 21 days after infection GFP(+) | 28 days after infection puro$^r$ | 28 days after infection GFP(+) |
|---|---|---|---|---|---|---|---|---|---|---|
| 0.5 | 0.5 | 0.5 | 0.5 | | $1 \times 10^4$ | 20.0 | 209 | 12 | many | 94 |
| | | | | | $1 \times 10^4$ | 5.0 | 1354 | 290 | many | 423 |
| | | | | | $1 \times 10^4$ | 1.0 | 171 | 64 | many | 199 |
| | 0.5 | 0.5 | 0.5 | 0.5 | $1 \times 10^5$ | 20.0 | 34 | 9 | 57 | 45 |
| | | | | | $1 \times 10^5$ | 5.0 | 200 | 144 | 300 | 298 |
| | | | | | $1 \times 10^5$ | 1.0 | 120 | 38 | 90 | 84 |
| | | | | 2 | $1 \times 10^4$ | 20.0 | 0 | 0 | 0 | 0 |
| | | | | | $1 \times 10^4$ | 5.0 | 0 | 0 | 0 | 0 |
| | | | | | $1 \times 10^4$ | 1.0 | 0 | 0 | 0 | 0 |

TABLE 2

| c-Myc (mL) | Oct3/4 (mL) | Sox2 (mL) | Klf4 (mL) | mock (mL) | Number of cells resown | Oxygen concentration (%) | 21 days after infection | | 28 days after infection | |
|---|---|---|---|---|---|---|---|---|---|---|
| | | | | | | | puro$^r$ | GFP(+) | puro$^r$ | GFP(+) |
| 0.5 | 0.5 | 0.5 | 0.5 | | $2 \times 10^4$ | 20.0 | 84 | 2 | 102 | 13 |
| | | | | | $2 \times 10^4$ | 5.0 | 140 | 19 | 210 | 38 |
| | | | | | $2 \times 10^4$ | 1.0 | 51 | 10 | 59 | 25 |
| | 0.5 | 0.5 | 0.5 | 0.5 | $1 \times 10^5$ | 20.0 | 0 | 0 | 0 | 0 |
| | | | | | $1 \times 10^5$ | 5.0 | 2 | 2 | 3 | 3 |
| 0.5 | 0.5 | | 0:5 | 0.5 | $1.5 \times 10^5$ | 20.0 | many | 0 | many | 0 |
| | | | | | $1.5 \times 10^5$ | 5.0 | many | 0 | many | 4 |
| | | | | 2 | $2 \times 10^4$ | 20.0 | 0 | 0 | 0 | 0 |
| | | | | | $2 \times 10^4$ | 5.0 | 0 | 0 | 0 | 0 |
| | | | | | $2 \times 10^4$ | 1.0 | 0 | 0 | 0 | 0 |

TABLE 3

| c-Myc (mL) | Oct3/4 (mL) | Sox2 (mL) | Klf4 (mL) | mock (mL) | Number of cells resown | Oxygen concentration (%) | 21 days after infection | | 28 days after infection | |
|---|---|---|---|---|---|---|---|---|---|---|
| | | | | | | | puro$^r$ | GFP(+) | puro$^r$ | GFP(+) |
| 0.5 | 0.5 | 0.5 | 0.5 | | $2 \times 10^4$ | 20.0 | 646 | 75 | many | 209 |
| | | | | | $2 \times 10^4$ | 5.0 | 566 | 261 | many | 404 |
| | | | | | $2 \times 10^4$ | 1.0 | 464 | 142 | many | 251 |
| | 0.5 | 0.5 | 0.5 | 0.5 | $1 \times 10^5$ | 20.0 | 26 | 2 | 15 | 12 |
| | | | | | $1 \times 10^5$ | 5.0 | 64 | 29 | 52 | 51 |
| 0.5 | 0.5 | | 0.5 | 0.5 | $1.5 \times 10^5$ | 20.0 | 28 | 0 | many | 0 |
| | | | | | $1.5 \times 10^5$ | 5.0 | 84 | 0 | many | 0 |
| | | | | 2 | $2 \times 10^4$ | 20.0 | 0 | 0 | 0 | 0 |
| | | | | | $2 \times 10^4$ | 5.0 | 0 | 0 | 0 | 0 |
| | | | | | $2 \times 10^4$ | 1.0 | 0 | 0 | 0 | 0 |

Taken together, Under 5% oxygen, the GFP-positive colonies derived from four-factor transduced MEFs increased 7.4-fold on day 21 and 3.1-fold on day 28 than those under the normal oxygen condition, and saimly those from three-factor transduced MEFs increased 20-fold on day 21 and 7.6-fold on day 28 under 5% oxygen (FIG. 14 a), b), c) and d)). Moreover, hypoxic treatment increased the percentage of GFP-positive colonies in total colonies from four- or three-factor transduced MEFs (FIG. 14 e) and f)). The GFP-positive colonies derived after hypoxic treatment was comparable in morphology and size to those derived under normoxic conditions (FIG. 16). Alkaline phosphatase staining showed that cultivation under 5% oxygen increased the number of colonies with a positive alkaline phosphatase activity (FIG. 17).

To investigate whether GFP-positive cells were detected earlier or not, the four-factor transduced MEFs were cultivated under 20% oxygen or under 5% oxygen with or without 2 mM valproic acid (VPA) from day 5 to day 9 posttransduction, and were subjected to flow cytometric analysis on day 9. Retroviral expression of four factors induced 0.01% of the cells to become GFP-positive on day 9 posttransduction. Treating the four-factor transduced MEFs for four days with hypoxia or with VPA increased the percentage of GFP-positive cells to 0.40% and 0.48%, respectively. Moreover, co-treatment with hypoxia and VPA increased the percentage of GFP-positive cells to 2.28%. These data suggest that GFP-positive cells can be detected earlier and that the hypoxic culture has synergistic effect with VPA (FIG. 15 a), b), d) and e)).

Subsequently, the effect of hypoxic culture was examined using adult human dermal fibroblasts (HDFs). Four factors (OCT3/4, SOX2, KLF4, c-MYC) or three factors (OCT3/4, SOX2, KLF4), all derived from humans, were introduced by means of retroviruses, as described in Cell, 131, 861-872 (2007). Six days after the viral infection, the cells were recovered and re-sown onto feeder cells. The feeder cells used were SNL cells treated with mitomycin C to terminate their cell division [McMahon, A. P. & Bradley, A. Cell 62, 1073-1085 (1990)]. The following day, the cells were brought into cell culture with a medium prepared by adding 4 ng/ml recombinant human bFGF (WAKO) to a primate ES cell culture (ReproCELL).

Between day 7 after the infection and colony counting days (days 24 and 32 after the infection), the cells were cultured in an incubator set at a normal oxygen concentration (20%) or low oxygen concentrations (5%, 1%). The results are shown in Table 4. When the four factors were introduced, the efficiency of establishment of iPS cells rose at an oxygen concentration of 5%, compared with the normal oxygen concentration. Meanwhile, when the oxygen concentration was 1% or when the three factors were introduced, no iPS cells were obtained under the culture conditions examined in this experiment, which involved the maintenance of cells in hypoxic conditions for a long time. This suggests that it may be necessary to have a shorter duration of cell culture under hypoxic conditions with the use of severer hypoxic conditions, such as an oxygen concentration of 1%, or with the introduction of three factors, which essentially produces lower efficiency of establishment of iPS cells than with four factors.

TABLE 4

| c-Myc (mL) | Oct3/4 (mL) | Sox2 (mL) | Klf4 (mL) | mock (mL) | Number of cells resown | Oxygen concentration (%) | 24 days after infection | | 32 days after infection | |
|---|---|---|---|---|---|---|---|---|---|---|
| | | | | | | | All colonies | ES-like cell colonies | All colonies | ES-like cell colonies |
| 1 | 1 | 1 | 1 | | $1 \times 10^5$ | 20.0 | 32 | 4 | 68 | 9 |
| | | | | | $1 \times 10^5$ | 5.0 | 31 | 10 | 56 | 16 |
| | | | | | $1 \times 10^5$ | 1.0 | 0 | 0 | 3 | 0 |
| | 1 | 1 | 1 | 1 | $4 \times 10^5$ | 20.0 | 0 | 0 | 1 | 0 |
| | | | | | $4 \times 10^5$ | 5.0 | 0 | 0 | 3 | 0 |
| | | | | 4 | $1 \times 10^5$ | 20.0 | 0 | 0 | 0 | 0 |
| | | | | | $1 \times 10^5$ | 5.0 | 0 | 0 | 0 | 0 |
| | | | | | $1 \times 10^5$ | 1.0 | 0 | 0 | 0 | 0 |

Example 2

Effect (2) of the Hypoxic Culture Method on the Establishment of iPS Cells

An experiment was performed to determine whether the hypoxic culture method was effective with introduction of the two genes Oct3/4 and Klf4 alone. The experiment used MEFs from the same Nanog reporter mouse as in Example 1. In the same manner as Example 1, retroviral expression vectors (pMXs-Oct3/4, pMXs-Klf4) were infected to the MEFs. On day 4 after the infection, $1 \times 10^5$ cells of the MEFs were sown to a 100 mm dish having feeder cells sown in advance. Thereafter every 2 days, the ES cell culture medium was replaced with a fresh supply.

Figure 1:
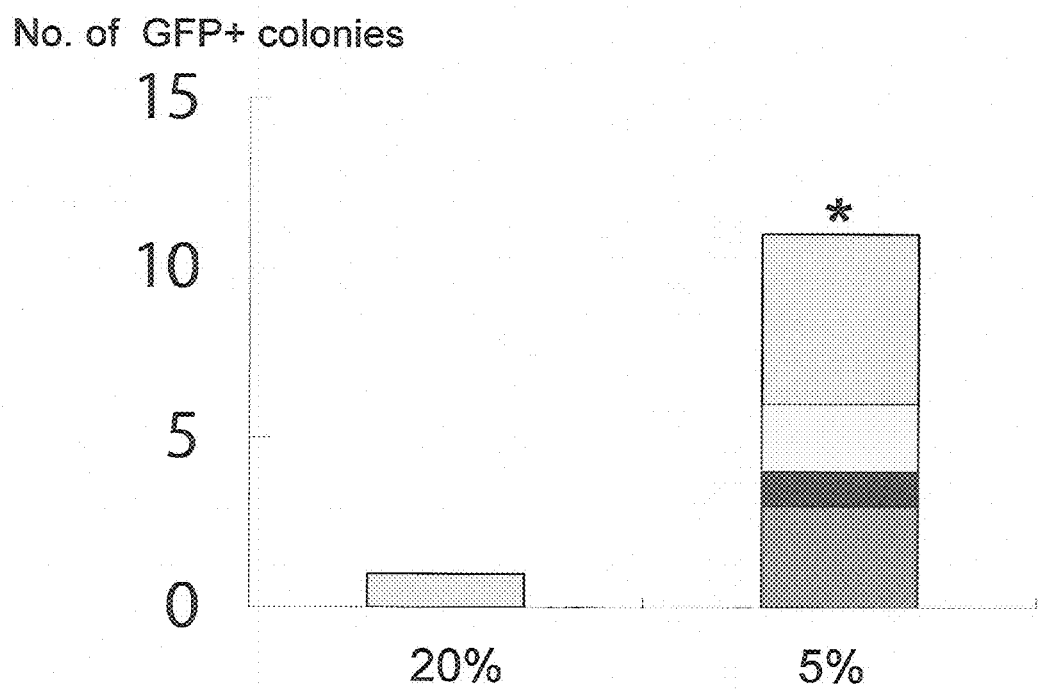
FIG. 1 is a graphic representation comparing the numbers of iPS cell colonies (GFP-positive colonies) of established by introducing the two genes Oct3/4 and Klf4 into MEFs at a normal oxygen concentration (20%) and a low oxygen concentration (5%) (*$p<0.05$).

Between days 5 and 14 after the infection, the cells were cultured in an incubator (Thermo Scientific) set at a normal oxygen concentration (20%) or a low oxygen concentration (5%). The culture was continued, without drug selection, until day 28, when GFP-positive colonies were counted. The results are shown in FIG. 1. Four independent experiments were performed. When the oxygen concentration was 20%, colonies emerged in only one of the four experiments, whereas when the oxygen concentration was 5%, colonies emerged in all of the four experiments. As shown in FIG. 1, the number of GFP-positive colonies increased significantly (*$p<0.05$) with cell culture at an oxygen concentration of 5%, compared with 20% oxygen concentration; the hypoxic culture was found to be effective in raising the efficiency of establishment of iPS cells.

Figure 2:
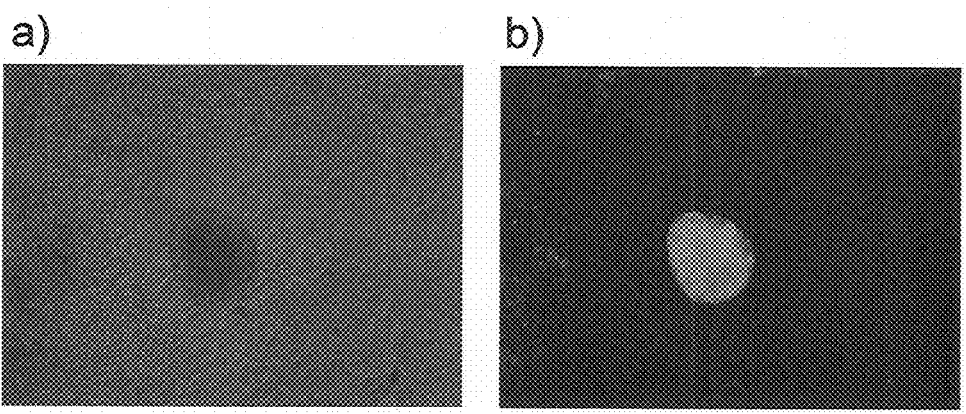
FIG. 2 shows images of iPS cell colony (GFP-positive colony) established by introducing the two genes Oct3/4 and c-Myc into MEFs [a) a phase-contrast image; b) an image of GFP-positive colony].

A further experiment was performed to determine whether the hypoxic culture method was also effective with transfer of the two genes Oct3/4 and c-Myc. The experiment was performed in the same manner as with Oct3/4 and Klf4 described above using Nanog-MEF. Between days 5 and 14 after the infection, the cells were cultured in an incubator (Thermo Scientific) set at a normal oxygen concentration (20%) and a low oxygen concentration (5%). The culture was continued, without drug selection, until day 42, when GFP-positive colonies were examined. As a result, when the culture was performed at a normal oxygen concentration (20%), no GFP-positive colonies emerged, whereas when the culture was performed at a low oxygen concentration (5%), colonies emerged (FIG. 2). These findings show that the efficiency of establishment of iPS cells can be improved by culturing the starting cell under hypoxic conditions even with introduction of the two genes Oct3/4 and c-Myc.

Example 3

Expression of Markers for Undifferentiated State in Mouse iPS Cells

Figure 3:
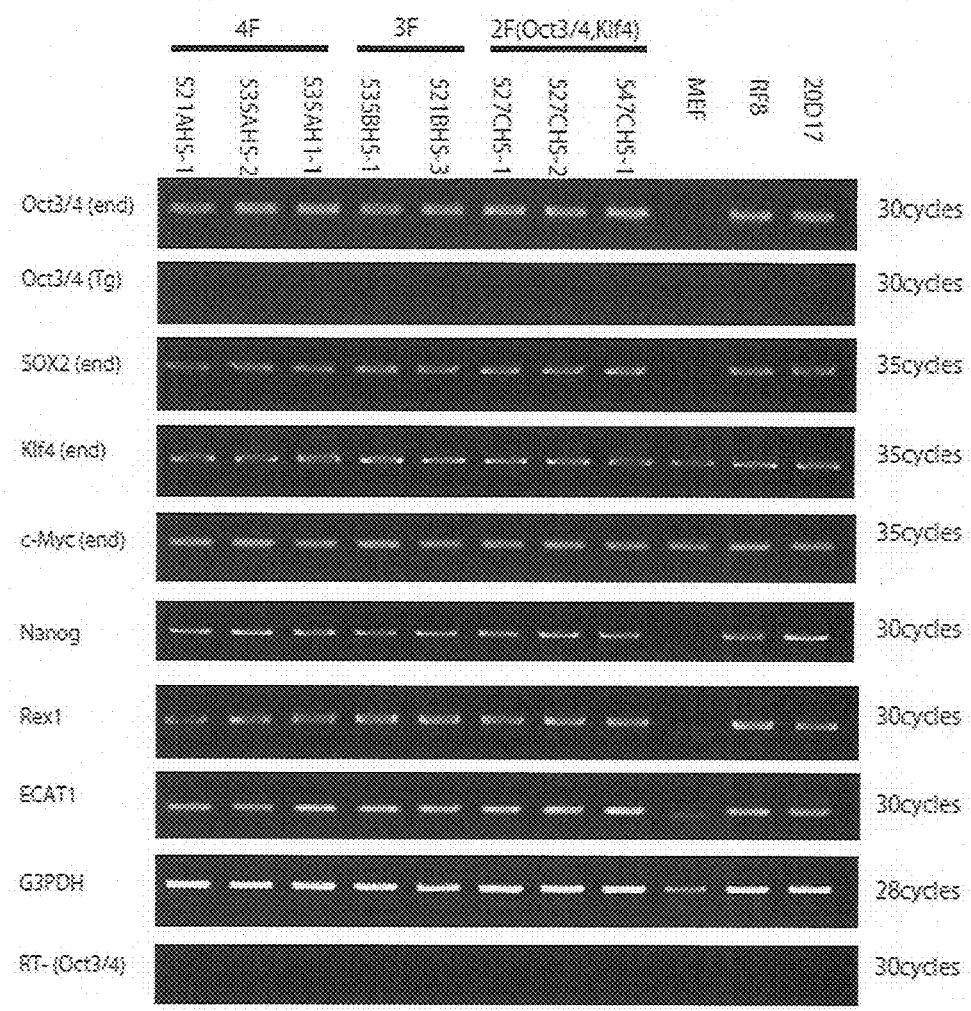
FIG. 3 is a photographic representation of results of RT-PCR performed using RNAs from iPS cells established at low oxygen concentrations. The expression of the markers for undifferentiated state Oct3/4(end), Sox2(end), Klf4(end), c-Myc(end), Nanog, Rex1, and ECAT1, and the expression of introduced exogenous Oct3/4(Tg) were examined. The samples corresponding to the respective lanes are as follows:
521AH5-1 and 535AH5-2: 4 genes (Oct3/4, Klf4, Sox2, c-Myc) were introduced; cells were cultured at 5% oxygen concentration
535AH1-1: 4 genes were introduced; cells were cultured at 1% oxygen concentration
535BH5-1 and 521BH5-3: 3 genes (Oct3/4, Klf4, Sox2) were introduced; cells were cultured at 5% oxygen concentration
527CH5-1, 527CH5-2 and 547CH5-1: 2 genes (Oct3/4, Klf4) were introduced; cells were cultured at 5% oxygen concentration
RF8: Control ES cells
20D17: Control Nanog-iPS cells [*Nature*, 448, 313-317 (2007)]
The numerical figure on the right side of each pannel indicates the number of PCR cycles.

The expression of markers for undifferentiated state in the MEF-derived iPS cells established in Examples 1 and 2 was examined by RT-PCR analyses using the Rever Tra Ace kit (Takara). The sequences of the primers used are shown by SEQ ID NO:1-18. The results of the RT-PCR are shown in FIG. 3.

The iPS cells established with introduction of four genes (Oct3/4, Klf4, Sox2, c-Myc), three genes (Oct3/4, Klf4, Sox2), or two genes (Oct3/4, Klf4) by cell culture at low oxygen concentrations (5%, 1%) all expressed genes that are expressed specifically in ES cells, i.e., Oct3/4, Sox2, Klf4, c-Myc, Nanog, Rex1, and ECAT1, the amounts expressed being equivalent to those in mouse ES cells (RF8) and iPS cells established with four genes in the past [20D17: *Nature*, 448, 313-317 (2007)]. Because no expression of the Oct3/4 gene introduced (Oct3/4(Tg)) was observed, it was demonstrated that silencing occurred. Based on these results, the cells established under the hypoxic conditions were identified as iPS cells.

Example 4

Potential of Established iPS Cells for Teratoma Formation

Mouse iPS cells established with Oct3/4 and Klf4 at a low oxygen concentration (5%) (527CH5-2) were allowed to form teratomas, as described in *Cell*, 126, 663-676 (2006). Specifically, $1 \times 10^6$ iPS cells were subcutaneously injected into immunodeficient mice; 4 weeks later, the emerging teratomas were isolated (upper pannels in FIG. 4). Each teratoma was shredded and fixed in PBS(−) containing 4% formaldehyde. Paraffin-embedded tissue was sliced and stained with hematoxylin-eosin. The results are shown in the lower pannels in FIG. 4. Histologically, the tumor was composed of a plurality of kinds of cells, with cartilage tissue, endodermal epithelial tissue, muscle tissue, and keratinized epithelial tissue observed. Thus, the pluripotency of the iPS cells was demonstrated.

Example 5

Creation of Chimeric Mice

The iPS cells established with introduction of two, three or four genes at a low oxygen concentration (5%) in Examples 1 and 2 were microinjected into blastocysts from ICR mice. As a result, adult chimeras were produced. The results are shown in FIG. 5.

Example 6

The Karyotype of iPS Cell Lines

The karyotype of iPS cell lines derived after hypoxic treatment (521AH5-1 and 527CH5-1) in Examples 1 and 2, and these cell lines showed normal karyotypes (FIG. 18).

Example 7

Effects of Duration of Hypoxic Culture on Establishment of Human iPS Cells

The effects of the starting time and duration of cell culture under hypoxic conditions (5%) on the efficiency of establishment of human iPS cells were examined. The somatic cells used were adult human dermal fibroblasts (adult HDFs). The time schedule for the hypoxic culture is shown in FIG. 6. First, the HDFs were allowed to express the mouse ecotropic virus receptor Slc7a1 gene using a lentivirus as described in Cell, 131, 861-872 (2007). Four factors (Oct3/4, Sox2, Klf4, c-Myc) or three factors (Oct3/4, Sox2, Klf4), all derived from humans, were introduced into these cells ($8 \times 10^5$ cells) by means of retroviruses, as described in Cell, 131, 861-872 (2007). Six days after the viral infection, the cells were recovered and re-sown onto feeder cells (in case of introduction of four genes, $1 \times 10^5$ cells/100 mm dish; in case of introduction of three genes, $5 \times 10^5$ cells/100 mm dish). The feeder cells used were SNL cells treated with mitomycin C to terminate their cell division [McMahon, A. P. & Bradley, A. Cell 62, 1073-1085 (1990)]. The following day, cell culture was started using a medium prepared by adding 4 ng/ml recombinant human bFGF (WAKO) to a primate ES cell culture medium (ReproCELL).

The cell culture was continued under six conditions: (1) at a normal oxygen concentration (20%) until day 40 after the infection, or at a low oxygen concentration (5%) for 1 week (2), 1.5 weeks (3), 2 weeks (4), or 3 weeks (5) from day 7 after the infection, and then at a normal oxygen concentration (20%) until day 40 after the infection, and (6) at a low oxygen concentration (5%) between days 7 and 40 after the infection. Also examined were the results obtained by pre-culturing the cells at a low oxygen concentration (5%) between the day after the infection and their re-sowing onto the feeder cells, and further culturing them under any of the conditions (1) to (6) described above. The iPS cell colonies that emerged by days 24, 32 and 40 after the infection were counted. The results of these three counts are shown together in FIG. 7.

With introduction of four genes, the efficiency of establishment of iPS cells was higher when the cells were cultured under any of the low oxygen concentration conditions (2) to (6) described above, compared with a normal oxygen concentration (20%). Furthermore, even with pre-culture at a low oxygen concentration, an effect was observed in increasing the efficiency of establishment of iPS cells. Images of colonies obtained on day 40 after the infection with introduction of four genes are shown in FIG. 8.

With transfer of three genes, a larger number of iPS cells were established when pre-culture was performed at a low oxygen concentration, compared with a normal oxygen concentration (FIG. 7).

With introduction of four genes (Oct3/4, Klf4, Sox2, c-Myc), three independent experiments were performed under the conditions (1), (2), (4), (5) and (6) described above. The results are shown together in FIG. 9. In all cases, the efficiency of establishment of iPS cells rose when cultivation was performed at a low oxygen concentration (5%), compared with a normal oxygen concentration (20%). In particular, a remarkable effect was obtained by cell culture at a low oxygen concentration for 2 weeks or more from day 7 after the infection.

Example 8

Expression of Markers for Undifferentiated State in Human iPS Cells

The expression of markers for undifferentiated state in the adult HDF-derived iPS cells established in Example 7 was examined by RT-PCR analyses using the Rever Tra Ace kit (Takara). The sequences of the primers used are shown by SEQ ID NO:19-36; the results of the RT-PCR are shown in FIG. 10. The iPS cells established with introduction of four genes (Oct3/4, Klf4, Sox2, c-Myc) or three genes (Oct3/4, Klf4, Sox2) by cell culture at a low oxygen concentration (5%) all expressed genes that are expressed specifically in ES cells, i.e., Oct3/4, Sox2, Klf4, c-Myc, Nanog, Rex1, GDF3 and ESG1, the amounts expressed being equivalent to those in iPS cells established with four genes in the past [201B2: Cell, 131, 861-872 (2007)]. Based on these results, the cells established at the low oxygen concentration were identified as iPS cells.

Furthermore, these iPS cells were strongly positive for alkaline phosphatase, and immunocytological staining showed that all of the iPS cells expressed Nanog, SSEA3 and SSEA4 (FIG. 11).

Example 9

In Vitro Differentiation Induction

Human iPS cells established by introducing the four genes Oct3/4, Klf4, Sox2, and c-Myc and culturing the starting cells at 5% oxygen concentration between day 7 to day 40 after the infection (70AH5-2, 70AH5-6) were sown to low-binding dishes, and cultured as described in Cell, 131, 861-872 (2007) for 8 days to form embryoid bodies (EB) (100 mm dishes). After being cultured for 8 days, the embryoid bodies were stained using antibodies against the endodermal cell differentiation marker α-fetoprotein (R&D systems), the mesodermal cell differentiation markers smooth muscle actin (DAKO), Desmin (NeoMarkers) and Vimentin (Santa Cruz), and the ectodermal differentiation markers βIII-tubulin (Chemicon) and GFAP (DAKO). The results are shown in FIG. 12. This staining confirmed the expression of these markers, demonstrating that the human iPS cells established possessed the potential for tridermic differentiation.

Example 10

Potential for Teratoma Formation of Established iPS Cells

Human iPS cells established by introducing four genes and culturing the starting cells at 5% oxygen concentration (70AH5-2) were examined for the potential for teratoma formation. The human iPS cells (70AH5-2) were cultured in a primate ES cell culture medium (ReproCELL) supplemented with recombinant human bFGF (4 ng/ml) and the Rho kinase inhibitor Y-27632 (10 µM). After 1 hour, the cells were treated with collagen IV and collected, after which they were recovered via centrifugation, and suspended in DMEM/F12 supplemented with Y-27632 (10 µM). A quarter amount of the cells that had become confluent (100 mm dish) was injected into the testis of an SCID mouse. After 9 weeks, the resulting tumor was shredded and fixed in PBS(−) containing 4% formaldehyde. Paraffin-embedded tissue was sliced and stained with hematoxylin-eosin. The results are shown in FIG. 13. Histologically, the tumor was composed of a plurality of kinds of cells, with nervous epithelial tissue, retinal epithelial tissue, osteoid tissue, smooth muscle tissue, and endodermal epithelial tissue observed. Thus, the pluripotency of the iPS cells was demonstrated.

Example 11

Effect of the Hypoxic Culture on Proliferation, Survival and Gene Expression

Flow cytometric analysis using annexin V demonstrated that hypoxic culture had no protective effect on mouse ES cells or on four-factor transduced MEFs (FIG. 19). Furthermore, hypoxic cultivation showed no effect on proliferation of mouse ES cells (FIG. 20 *a*)). Although hypoxic incubation from day 1 today 4 posttransduction had no significant effect on proliferation of mock transduced MEFs, it had significant effect on four-factor transduced MEFs (FIG. 20 *b*)). To investigate the expression profile of cells in reprogramming process, microarray analysis and quantitative real-time RT-PCR were performed. Microarray analysis of four-factor transduced MEFs cultivated under hypoxic and normoxic conditions from day 1 to day 4 showed that 73.2% of ES cell-specific genes (765 genes out of 1045 total genes) were up-regulated and 85.8% of MEF-specific genes (980 genes out of 1142 total genes) were down-regulated in the cells treated with hypoxia (FIG. 21 *a*) and *b*)). Moreover, quantitative real-time RT-PCR analysis demonstrated that expression of endogenous Oct3/4 and Nanog increased 3.4-fold and 2.1-fold respectively in four-factor transduced MEFs after hypoxic treatment of three days (FIG. 22 *a*) and *b*)).

To rule out the possibility that hypoxia enhances iPS cell generation by stimulating STO cells, growth situation of iPS cells were examined under hypoxic cultivation without the feeder layer of STO cells. FIG. 23 shows that cultivation under 5% oxygen increased the number of GFP-positive colonies, suggesting that hypoxic enhancement of reprogramming was not mediated by STO cells.

Example 12

Establishment of iPS Cells by Transient Transfection of Expression Plasmid Vector Under the Hypoxic Culture Generation of iPS cells with plasmid transfection was performed as previously described (Okita, K, et al. Science 322, 949-953, (2008)). Briefly, MEFs, which contain Nanog-GFP-IRES-Puror reporter, were seeded at $1.0 \times 10^5$ cells/well in 6-well plates (Day0). On day 1, 3, 5, and 7, the cells were transfected with pCX-OKS-2A and pCX-c-Myc, and on day 9, the cells, were harvested with trypsin and were reseeded onto 100-mm dishes with STO feeder cells. On day 25, the number of GFP-positive colonies were counted. For hypoxic treatment, the cells were cultivated under 5% oxygen, from day 10 to day 24.

Table 5 shows that hypoxic cultivation increased the number of GFP-positive colonies by 2.0-fold.

TABLE 5

| Exp. No. | Cell number | O2 concentration | GFP(+) colonies | Total colonies |
|---|---|---|---|---|
| Exp 1 | $1 \times 10^6$ | 20% | 3 | 18 |
|  |  | 5% | 7 | 32 |
| Exp 2 | $1 \times 10^6$ | 20% | 1 | 2 |
|  |  | 5% | 2 | 2 |
| Exp 3 | $1 \times 10^6$ | 20% | 23 | 61 |
|  |  | 5% | 35 | 62 |

Example 13

Establishment of iPS Cells by Piggyback Transfection System Under the Hypoxic Culture Direct reprogramming with piggyback (PB) transposition was performed as previously described with some modifications (Woltjen et al., Nature; 458: 766-70, (2009)). Briefly, MEFs, which contain Nanog-GFP-IBES-Puror reporter, were seeded at $1.0 \times 10^5$ cells/well in 6-well plates. After 24h culture, Fugene HD (Roche, Switzerland) was used to transfect cells with PB-TET-MKOS, PB-CA-rtTA Adv, and PB transposase expressing vector. After 24h, the media was replaced with doxycycline-containing media (1.5 ug/ml) (Day 0). The cells were cultivated under hypoxic or normoxic conditions, and the number of GFP-positive colonies were counted on day 12. PB-TET-MKOS and PB-CA-rtTA adv were provided from Addgene (Addgene plasmid 20910 and 20959). The PB transposase construct was amplified by PCR from pBSII-IFP2-orf (a generous gift from Dr. Malcolm J. Fraser, Jr, University of Notre Dame), and was inserted into the expression vector driven by CAG-promoter (pCX-EGFP).

FIG. 24 shows that hypoxic treatment for five and ten days increased the number of GFP-positive colonies by 2.9-fold and 4.0-fold, respectively. These data suggest that hypoxia can increase the efficiency of iPS generation by non-viral vectors such as piggybac transposition system.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on U.S. provisional patent application Nos. 61/084,842, 61/141,177 and 61/203,931, the contents of which are hereby incorporated by reference.

Then invention claimed is:

1. A method of improving the efficiency of establishment of mouse or human induced pluripotent stem (iPS) cells, comprising:
   a) introducing into mouse or human somatic cells an expression vector or expression vector expression vectors comprising nucleic acids encoding any of the following (i) to (ii):
   (i) Oct3/4, Klf4 and Sox2,
   (ii) Oct3/4, Klf4, Sox2 and c-Myc, and
   b) culturing the somatic cells from a) in ES cell culture medium, under hypoxic conditions wherein the oxygen concentration is 5%,
   thereby improving the efficiency of the establishment of iPS cells compared to the establishment efficiency of mouse or human iPS cells produced by the same method at an atmospheric concentration of oxygen.

2. The method according to claim 1, comprising the further step that valproic acid is used to improve the efficiency.

3. The method according to claim 1, wherein culturing somatic cells under hypoxic conditions is performed for more than 3 days after introducing the expression vector or vectors into the somatic cells.

4. The method according to claim 1 wherein the iPS cell is a mouse iPS cell.

5. The method according to claim 1 wherein the iPS cell is a human iPS cell.

6. The method according to claim 1 wherein the mouse or human somatic cells are fibroblasts.

7. A method of producing a mouse or human induced pluripotent stem (iPS) cell, comprising:
   a) introducing into mouse or human somatic cells an expression vector or expression vectors comprising nucleic acids encoding any of the following (i) to (ii):
   (i) Oct3/4, Klf4 and Sox2,
   (ii) Oct3/4, Klf4, Sox2 and c-Myc, and
   b) culturing the somatic cells from a) in ES cell culture medium, under hypoxic conditions wherein the oxygen concentration is 5%,
   thereby producing a mouse or human iPS cell, wherein the efficiency of producing said mouse or human iPS cells is improved compared to the production efficiency of a mouse or human iPS cell produced by the same method at an atmospheric concentration of oxygen.

8. The method according to claim 7, comprising the further step that said somatic cell is contacted with valproic acid.

9. The method according to claim 7, wherein culturing somatic cells under hypoxic conditions is performed for more than 3 days after introducing the expression vector or vectors into the somatic cells.

10. The method according to claim 7, wherein the iPS cell is a mouse iPS cell.

11. The method according to claim 7, wherein the iPS cell is a human iPS cell.

12. The method according to claim 7, wherein the somatic cell is a fibroblast.

13. A method for improving the efficiency of establishment of mouse induced pluripotent stem (iPS) cells, comprising:

a) introducing into mouse somatic cells an expression vector or expression vectors comprising nucleic acids encoding any of the following (i) to (iv):
(i) Oct3/4, Klf4 and Sox2,
(ii) Oct3/4, Klf4, Sox2 and c-Myc,
(iii) Oct3/4 and Klf4,
(iv) Oct3/4 and c-Myc, and
b) culturing the somatic cells from a) in ES cell culture medium, under hypoxic conditions, wherein the oxygen concentration is 1-5%,
thereby improving the efficiency of the establishment of iPS cells compared to the efficiency of establishment of mouse iPS cells produced by the same method at an atmospheric concentration of oxygen.

14. A method of improving the efficiency of establishment of reprogrammed mouse or human cells, comprising:
a) introducing into mouse or human somatic cells an expression vector or expression vectors comprising nucleic acids encoding any of the following (i) to (ii):
(i) Oct3/4, Klf4 and Sox2,
(ii) Oct3/4, Klf4, Sox2 and c-Myc, and
b) culturing the somatic cells from a) in ES cell culture medium, under hypoxic conditions wherein the oxygen concentration is 5%,
thereby improving the efficiency of the establishment of reprogrammed mouse or human cells compared to the efficiency of establishment of reprogrammed mouse or human cells produced by the same method at an atmospheric oxygen concentration, and
wherein the reprogrammed mouse or human cells form ES-like colonies and are in a more undifferentiated state than the mouse or human somatic cells.

* * * * *